(12) United States Patent
Rajasekaran

(10) Patent No.: US 9,636,340 B2
(45) Date of Patent: May 2, 2017

(54) KINASE INHIBITORS

(71) Applicant: Ayyappan K. Rajasekaran, Glen Mills, PA (US)

(72) Inventor: Ayyappan K. Rajasekaran, Glen Mills, PA (US)

(73) Assignee: Ayyappan K. Rajasekaran, Glen Mills, PA (US)

( * ) Notice: Subject to any disclaimer, the term of this patent is extended or adjusted under 35 U.S.C. 154(b) by 0 days.

(21) Appl. No.: 14/537,980

(22) Filed: Nov. 11, 2014

(65) Prior Publication Data

US 2015/0140071 A1    May 21, 2015

Related U.S. Application Data

(60) Provisional application No. 61/903,154, filed on Nov. 12, 2013.

(51) Int. Cl.
*A61K 9/127* (2006.01)
*A61K 31/4741* (2006.01)
*A61K 47/48* (2006.01)

(52) U.S. Cl.
CPC .... *A61K 31/4741* (2013.01); *A61K 47/48215* (2013.01)

(58) Field of Classification Search
USPC .......................................................... 424/450
See application file for complete search history.

(56) References Cited

U.S. PATENT DOCUMENTS

| | | | |
|---|---|---|---|
| 5,384,022 A | 1/1995 | Rajasekaran | |
| 5,390,859 A | 2/1995 | Rajasekaran | |
| 5,411,872 A | 5/1995 | Rajasekaran et al. | |
| 5,521,184 A | 5/1996 | Zimmermann | |
| 6,410,550 B1 | 6/2002 | Coe et al. | |
| 6,444,673 B1 | 9/2002 | Cotrel et al. | |
| 6,596,746 B1 | 7/2003 | Das et al. | |
| 6,894,051 B1 | 5/2005 | Zimmermann et al. | |
| 7,125,875 B2 | 10/2006 | Das et al. | |
| 7,153,856 B2 | 12/2006 | Barrish et al. | |
| 8,114,874 B2 | 2/2012 | Zou et al. | |
| 8,287,851 B2 | 10/2012 | Wright et al. | |
| 8,293,756 B2 | 10/2012 | Bruneau | |
| 8,563,592 B2 | 10/2013 | Nuijen et al. | |
| 8,597,645 B2 | 12/2013 | Schneider et al. | |
| 8,623,373 B2 | 1/2014 | Zardi et al. | |
| 8,754,091 B2 | 6/2014 | Honigberg et al. | |
| 8,821,927 B2 | 9/2014 | Carter et al. | |
| 2005/0261220 A1 | 11/2005 | Krissansen et al. | |
| 2006/0069241 A1 | 3/2006 | Rajasekaran et al. | |
| 2006/0148688 A1 | 7/2006 | Rajasekaran et al. | |
| 2007/0237712 A1 | 10/2007 | Rajasekaran et al. | |
| 2007/0287706 A1* | 12/2007 | Dickson, Jr. ......... | C07D 215/22 514/230.5 |
| 2008/0255099 A1 | 10/2008 | De Munari et al. | |
| 2010/0330668 A1 | 12/2010 | Ratcliffe et al. | |
| 2013/0344075 A1 | 12/2013 | Krasnoperov et al. | |

FOREIGN PATENT DOCUMENTS

| | | |
|---|---|---|
| EP | 2530081 A2 | 12/2012 |
| EP | 2626355 A1 | 8/2013 |
| WO | 0018761 A1 | 4/2000 |

OTHER PUBLICATIONS

Wall (Bioorganic & Medicinal Chemistry Letters 18 (2008) 2097-2102).*
Dingledine (http://pubchem.ncbi.nlm.nih.gov/bioassay/1422#section=Top; Oct. 31, 2008).*
Pubchem (http://pubchem.ncbi.nlm.nih.gov/compound/3208330#section=Top; Dec. 26, 2015).*
Pubchem2 (http://pubchem.ncbi.nlm.nih.gov/substance/4197083#section=Top; Aug. 10, 2005).*
Asinex (http://www.asinex.com/libraries_gold_platinum.html; accessed Apr. 14, 2016).*
Alley (Cancer Research 48, 589-601, Feb. 1, 1988).*
Remington's Pharmaceutical Sciences, Fifteenth Edition, E. W. Martin (Mack Publishing Co., Easton, Pa., 1975).
Capdeville R, et al., "Glivec (STI571, imatinib), a rationally developed, targeted anticancer drug," Nature reviews Drug discovery 2002, 1(7):493-502.
O'Hare T, et al., "Bcr-Abl kinase domain mutations, drug resistance, and the road to a cure for chronic myeloid leukemia," Blood 2007, 110(7):2242-2249.
PubChem Compound: ASN 05548619—Compound Summary, National Center for Biotechnology Information, U.S. National Library of Medicine 8600 Rockville Pike, Bethesda, MD 20894, USA, <http://pubchem.ncbi.nlm.nih.gov/summary/summary.cgi?cid=3208330>, Jul. 25, 2013.
Research and Development Related to dasatinib (Sprycel™), KEI Research Note 2008:3, Jacqueline Lee, Aug. 1, 2008.
Drug carrier, Wikipedia Article, Sep. 23, 2014.
Excipient, Wikipedia Article, Sep. 24, 2014.
Imatinib, Wikipedia Article, Sep. 22, 2014.
PEGylation, Wikipedia Article, Sep. 23, 2014.

* cited by examiner

*Primary Examiner* — Devang Thakor
(74) *Attorney, Agent, or Firm* — Paul & Paul

(57) ABSTRACT

The disclosed molecules are inhibitors of Bcr-Abl and Src kinases. The molecules are cytotoxic to Gleevec resistant cells. Inhibitors of Bcr-Abl and Src kinases are used in the treatment of Chronic Myelogenous Leukemia among other diseases.

17 Claims, 6 Drawing Sheets
(1 of 6 Drawing Sheet(s) Filed in Color)

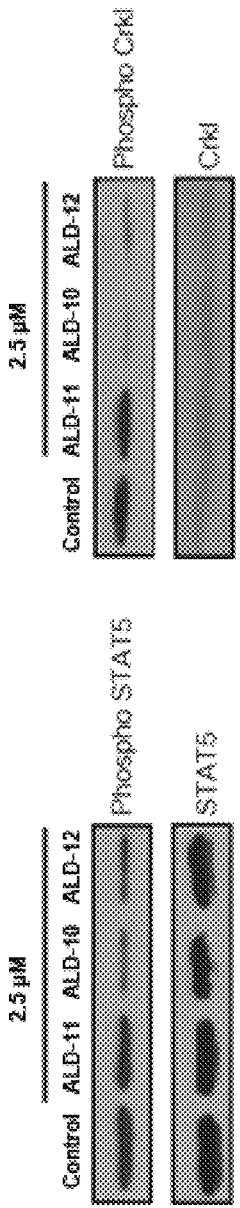
FIG. 7
FIG. 8
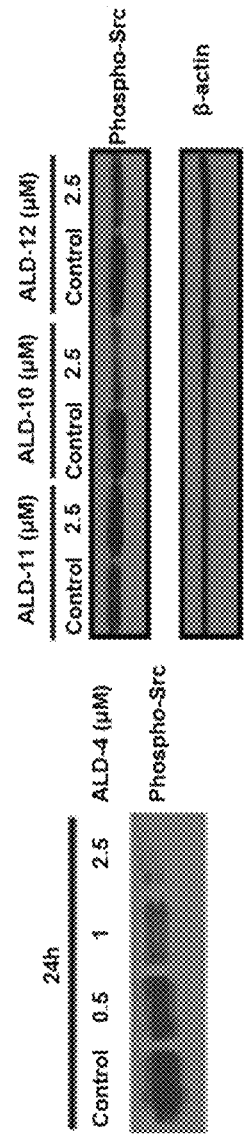
FIG. 9
FIG. 10

KINASE INHIBITORS

CROSS-REFERENCE TO RELATED APPLICATION

This application claims the benefit of the priority of U.S. Provisional Application No. 61/903,154, filed on Nov. 12, 2013, which is incorporated herein by reference in its entirety.

BACKGROUND OF THE INVENTION

1. Field of the Invention

The present invention relates to pharmacologically active formulations and their method of use as kinase inhibitors.

2. Description of the Prior Art

Chronic Myelogenous Leukemia (CML) is the most common leukemia in adults. In 2014, an estimated 5,980 new cases of chronic myeloid leukemia (CML) are expected to be diagnosed and 810 deaths due to CML in the US. CML is a disease of hematopoietic stem cells and is characterized by the presence of a Philadelphia chromosome, a fusion of the Abelson murine leukemia (Abl) gene on chromosome 9 with the breakpoint cluster region (Bcr) gene on chromosome 22. This chimeric chromosome generates the Bcr-Abl gene. The resultant oncoprotein is a tyrosine kinase which interacts with a variety of signaling proteins such as RAS, RAF, JUN kinase, MYC and STAT, that lead to cellular transformation or that are involved in signaling pathways implicated in cellular transformation or cancer cell development.

Previously, drug therapy for CML was limited to nonspecific agents such as busulfan, hydroxyurea, and interferon-alpha (INF-a). INF-a led to regression of the disease and improved survival but was hindered by a multitude of toxicities. Allogeneic stem cell transplantation (SCT) was a curative intervention but carried a high risk of morbidity and mortality. Further, SCT is only an option for patients with excellent performance status and an appropriate stem cell donor.

Small molecule tyrosine kinase inhibitors (TKIs) were developed to exploit the presence of the aberrantly expressed Bcr-Abl protein in CML cells. Presently, there are four commercially available TKIs for the treatment of CML; these include imatinib, dasatinib, nilotinib, and ponatinib. Imatinib mesylate (Gleevec or Glivec as it is known in Europe) was the first TKI to receive approval by the Food and Drug Administration (FDA) for the treatment of patients with CML. It acts via competitive inhibition at the ATP-binding site of the Bcr-Abl protein, which results in the inhibition of phosphorylation of Bcr-Abl involved in cell signal transduction.

Phosphorylation of Bcr-Abl activates this enzyme and induces downstream signaling which promotes cell proliferation. Activation of Bcr-Abl results in the phosphorylation of one of its key targets, STAT5, a transcription factor involved in leukemogenesis. Phosphorylated STAT5 acts as a docking site for the SH2 domain of CrkL. CrkL and STAT5 then form a complex that translocates to the nucleus and induces transcription of genes involved in cell proliferation and cell survival. Fish E N, et al., "Activation of a CrkL-stat5 signaling complex by type I interferons," *The Journal of biological chemistry* 1999, 274(2):571-573. Thus, STAT5 and CrkL are well established downstream targets of Bcr-Abl. Inhibition of Bcr-Abl with Gleevec (imatinib) reduces phosphorylation of both STAT5 and CrkL and attenuates their transcriptional activity. Capdeville R, et al., "Glivec (STI571, imatinib), a rationally developed, targeted anticancer drug," *Nature reviews Drug discovery* 2002, 1(7):493-502. However, mutations acquired in the Bcr-Abl gene during CML progression were found to disable Gleevec activity which then failed to inhibit the CML progression. New drugs are needed to treat patients who have developed resistance to Gleevec.

This problem led to the rational development of second generation TKIs with hopes they would effectively treat patients unable to continue on Imatinib therapy. Dasatinib is an oral, second generation TKI that is 350 times more potent than Imatinib in vitro. In addition, it is also known to inhibit the Src family of kinases, which may also be critical in cell signaling pathways in CML. Inhibitors of Src kinases are also used in the treatment of CML.

Dasatinib was also able to induce more major molecular responses (MMR) compared to the imatinib group. Nilotinib is a structural analog of imatinib, though its affinity for the ATP binding site on Bcr-Abl is up to 50 times more potent in vitro. Like dasatinib, nilotinib initially demonstrated the ability to induce hematologic and cytogenetic responses in patients who had failed imatinib.

Commercially available drugs based on the TKIs mentioned previously show drug resistance due to the point mutations in the kinase domain of Bcr-Abl, which arrests the activity of the TKIs. Second generation TKIs are developed to overcome most of the mutations that confer resistance to imatinib, though novel mutations rendering the leukemia resistant to dasatinib and/or nilotinib have emerged. O'Hare T, et al., "Bcr-Abl kinase domain mutations, drug resistance, and the road to a cure for chronic myeloid leukemia," *Blood* 2007, 110(7):2242-2249. One important mutation, the T315I, is known as the "gatekeeper" mutation, as it displays resistance to all currently available TKIs. Ponatinib, binds to the ATP binding pocket of the mutated Bcr-Abl and inhibits its activity. The FDA approved ponatinib for treatment of CML in 2012, but put a hold on its clinical use due to severe vascular toxicity. Since there were no other alternatives and due to desperate need for the treatment of Gleevec resistant CML patients, the FDA reapproved ponatinib in early 2014. Therefore, new therapies are needed to improve the outcome of this disease.

SUMMARY OF THE INVENTION

The small molecules according to the present invention are potent inhibitors of Bcr-Abl and Src kinases. These molecules are cytotoxic to Gleevec resistant cells. These molecules have the potential to treat Gleevec resistant CML.

This invention relates to formulations including quinolone, isoquinoline or quinazoline derivatives that are effective in the treatment of leukemia and methods for their use. The quinolone, isoquinoline, or quinazoline derivatives used in the present invention fall under the following formula:

Formula 1

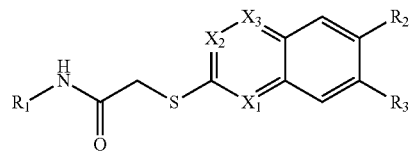

Wherein $R_1$ is selected from the group consisting of:

a) an aromatic ring substituted with a group selected from groups consisting of alkyl, alkoxy, —COOX$_4$ wherein X$_4$ is selected from H and a small alkyl group, nitrile groups, and halides, b) a heterocyclic ring substituted with a group selected from groups consisting of alkyl, alkoxy, —COOX$_4$ wherein X$_4$ is selected from H and a small alkyl group, nitrile groups, and halides, and c) a first ring selected from an aromatic ring and a heterocyclic ring, said first ring being linked to a second ring selected from an aromatic ring and a heteroaromatic ring, said first ring being substituted with a group selected from groups consisting of alkyl, alkoxy, —COOX$_4$ wherein X$_4$ is selected from H and a small alkyl group, nitrile groups, and halides.

$R_2$ is selected from H and OX$_5$ where X$_5$ is selected from a small alkyl group, the radical —CH$_2$—, and the radical —CH$_2$CH$_2$—. $R_3$ is selected from H and OX$_6$ where X$_6$ is selected from a small alkyl group, the radical —CH$_2$—, and the radical —CH$_2$CH$_2$—. $X_1$ is selected from —CH—, —C(=O)—, and N. $X_3$ is selected from —CH—, —C(=O)—, and N. $X_2$ is selected from N, —C(X$_7$)— where X$_7$ is selected from H, a small alkyl group, an alkoxy group, a nitrile, and a halide. The first ring may be directly linked to the second ring, or the first ring may be linked to the second ring through an amide bond.

The second ring may also be substituted with a group selected from groups consisting of alkyl, alkoxy, —COOX$_4$ wherein X$_4$ is selected from H and an alkyl group with one to ten carbon atoms, nitrile groups, and halides.

At least one of the first ring and the second ring may have a basic group attached to improve solubility.

$X_5$ may be selected from the radicals —CH$_2$— and —CH$_2$CH$_2$—, and X$_6$ may be selected from the radicals —CH$_2$— and —CH$_2$CH$_2$—, and X$_5$ and X$_6$ may be linked together to form a heterocycle.

A "small" alkyl group as used herein refers to an alkyl group with one to ten carbon atoms. Alternatively, the small alkyl group may have one to eight carbon atoms. As another alternative, the small alkyl group may have one to six carbon atoms. As yet another alternative, the small alkyl group may have one to four carbon atoms. As yet another alternative, the small alkyl group may have one to two carbon atoms. As yet another alternative, the small alkyl group may have one carbon atom.

In one aspect, the invention relates to a formulation for the treatment of Leukemia that includes a first component effective in the treatment of leukemia and a pharmaceutically acceptable delivery vehicle. The first component is selected from the group consisting of quinolones, isoquinolines, quinazolines, their derivatives, and mixtures thereof.

In another aspect, the first component is selected from the group consisting of compounds according to Formula 1, their derivatives, and mixtures thereof.

In yet another aspect, the first component is selected from the group consisting of dioxinoquinolines, their derivatives, and mixtures thereof.

In yet another aspect, the present invention relates to a formulation including a first component selected from the group consisting of compounds according to the formula as follows:

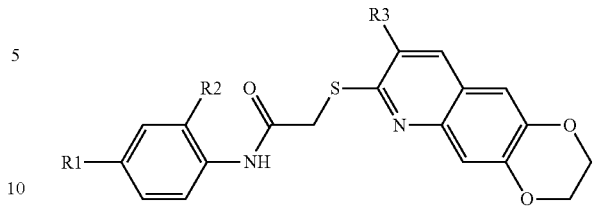

Formula 2 wherein R1 is selected from the group consisting of H, O—CH$_3$, and COO—CH$_3$, wherein R2 is selected from the group consisting of O—CH$_3$, CH$_3$, F, and H, wherein R3 is selected from the group consisting of CH$_2$—CH$_3$, CH$_3$, and C≡N, their derivatives, and mixtures thereof, and a pharmaceutically acceptable delivery vehicle, carrier, or excipient. The compounds of Formula 2 fall within the compounds of Formula 1. The compounds of Formula 2 fall within the category called [1,4]dioxino[2,3-g]quinolines or more simply, dioxinoquinolines.

It is an object of the present invention to provide a formulation having kinase inhibitor activity, wherein the formulation comprises a first component selected from the group consisting of compounds according to Formula 1, their derivatives, and mixtures thereof, and a pharmaceutically acceptable delivery vehicle.

It is another object of the present invention to provide a formulation having kinase inhibitor activity, wherein the formulation comprises a first component selected from the group consisting of compounds according to Formula 2, their derivatives, and mixtures thereof, and a pharmaceutically acceptable delivery vehicle.

It is an aspect of the present invention that the first component of the formulation includes modifications of the compounds according to Formula 1 and/or Formula 2. It is another aspect of the present invention that the first component of the formulation includes pharmaceutically acceptable modifications of the compounds of Formula 1 and/or Formula 2. It is yet another aspect of the present invention that the first component of the formulation includes mixtures of the compounds of Formula 1 and/or Formula 2 and pharmaceutically acceptable modifications of these compounds. It is an aspect of the present invention that the modifications of the compounds of Formula 1 and/or Formula 2 enhance uptake, enhance solubility, enhance efficacy, enhance retention, enhance pharmacokinetics, enhance selectivity, or reduce toxicity.

The term "pharmaceutically acceptable" as used herein in reference to an item means that the item is, within the scope of sound medical judgment, suitable for use in contact with the tissues of humans and lower animals without undue toxicity, irritation, allergic response, and the like, commensurate with a reasonable benefit/risk ratio, and effective for its intended use. When used in reference to items other than the primary, active drug or pharmaceutical agent, "pharmaceutically acceptable" also means that, within the scope of sound medical judgment and commensurate with a reasonable benefit/risk ratio, the item will not unduly impair the effectiveness of the primary, active drug or pharmaceutical agent for its intended use.

The terms "modifications" and "derivatives" are used interchangeably herein. The terms "modifications" and "derivatives" of the active pharmaceutical agents of the present invention refers to any compound, complex, or conjugate, or any covalently bonded, ionic bonded, hydrogen bonded, or otherwise associated adjunct of at least one of the active pharmaceutical agents of the present invention. The modifications dissociate or are metabolized so as to yield at least one of the active pharmaceutical agents of the present invention in vivo or within a target cell, or the modifying substituent may remain attached to the active pharmaceutical agent if the modification does not unduly impair the effectiveness of the active pharmaceutical agent. The modifications include modifications that are well known in the pharmaceutical art. Modifications to active pharmaceutical agents are typically made to enhance uptake, enhance solubility, enhance efficacy, enhance retention, enhance pharmacokinetics, enhance selectivity, or reduce toxicity. One type of modification includes the prodrug of an active pharmaceutical agent of the present invention, which is a substance that dissociates or is metabolized in vivo or in a target cell to yield a compound according to Formula 1 and/or Formula 2, for example, by hydrolysis in blood. Such a prodrug may have the benefit of longer shelf life or better transport through the gut. PEGylation is another modification within the scope of the present invention. PEGylation is the covalent attachment of polyethylene glycol (PEG) polymer chains to the active pharmaceutical agent. The covalent attachment of PEG to a drug can reduce immunogenicity and antigenicity, increase the hydrodynamic size (size in solution) of the agent which improves drug retention by reducing renal clearance, and improve solubility.

Examples of the modifications of the compounds of Formula 1 and/or Formula 2 suitable for use in the present invention include, without limitation, PEGylation products of the compounds of Formula 1 and/or Formula 2, encapsulated forms of the compounds of Formula 1 and/or Formula 2, encapsulated forms of the PEGylation products the compounds of Formula 1 and/or Formula 2, complexes of the compounds of Formula 1 and/or Formula 2, encapsulated forms of such complexes, conjugates of the compounds of Formula 1 and/or Formula 2, encapsulated forms of such conjugates, and combinations thereof.

Examples of the complexes of the compounds of Formula 1 and/or Formula 2 suitable for use in the present invention include, without limitation, protein-DNA complexes of the compounds of Formula 1 and/or Formula 2. Examples of the conjugates of the compounds of Formula 1 and/or Formula 2 suitable for use in the present invention include, without limitation, protein conjugates of said compounds.

It is an aspect of the present invention that each of the encapsulated forms of the compounds of Formula 1 and/or Formula 2, the encapsulated forms of the PEGylation products of such compounds, the encapsulated forms of the complexes of such compounds, and the encapsulated forms of the conjugates of such compounds may be made using any suitable encapsulation means and/or techniques. Examples of encapsulation means and/or techniques suitable for use in the present invention include, without limitation, encapsulation by micelles, encapsulation by liposomes, encapsulation by microspheres made of biodegradable polymer, encapsulation by albumin microspheres, encapsulation by synthetic polymers, encapsulation by nanofibers, encapsulation by multifunctional inorganic nanoparticles, encapsulation by erythrocytes, encapsulation by virosomes, encapsulation by dendrimers, and combinations thereof.

Examples of carriers and/or delivery vehicles suitable for use in liquid formulations according to the present invention include, without limitation, water, glycerin, or mixtures thereof. A plethora of further examples are provided herein below. Pharmaceutically acceptable delivery vehicle as used in the appended claims is a collective reference to vehicles, carriers, excipients, adjuvants, diluents, solvents, additives and delivery systems suitable for use in the present invention. Accordingly, pharmaceutically acceptable delivery vehicles include, but are not limited to, the many examples of drug delivery vehicles, carriers, excipients, adjuvants, diluents, solvents, additives and delivery systems provided herein.

It is an aspect of the present invention to provide a formulation that is cytotoxic to Gleevec-resistant leukemic cells derived from chronic myeloid leukemia. It is an aspect of the present invention to provide a formulation that is cytotoxic to leukemic cells derived from chronic myeloid leukemia that have developed resistance to current kinase inhibitor drug formulations including, but not limited to, imatinib, Dasatinib, nilotinib, or ponatinib.

It is an aspect of the present invention to provide a formulation for inhibiting kinase activity in cancer cells, such as for example leukemic cells, wherein the formulation comprises a first component selected from the group consisting of quinolones, isoquinolines, and quinazolines having a N-phenylacetamide substituent and also having an ortho substituent or an ortho and a para substituents relative to the N-phenylacetamide substituent, their derivatives, and combinations thereof, and a second component comprising, for example, a pharmaceutically acceptable carrier, delivery vehicle, or excipient.

It is another aspect of the present invention to provide a formulation wherein the derivatives are selected from the group consisting of PEGylation products of the quinolones, isoquinolines, and quinazolines, protein-DNA complexes of the quinolones, isoquinolines, and quinazolines, protein conjugates of the quinolones, isoquinolines, and quinazolines, prodrugs of the quinolones, isoquinolines, and quinazolines, any compound that yields the inhibitors of the present invention or their derivatives as a metabolite in living cells or in a living organism and combinations thereof.

It is yet another aspect of the present invention to provide a formulation including the quinolones, isoquinolines, and quinazolines and/or their derivatives and further comprising a pharmaceutically acceptable carrier selected from the group consisting of micelles, liposomes, microspheres made of biodegradable polymer, albumin microspheres, synthetic polymer encapsulants, nanofibers, multifunctional inorganic nanoparticles, erythrocytes, virosomes, dendrimers, and combinations thereof.

It is still another aspect of the present invention to provide a kinase inhibitor formulation including the quinolones, isoquinolines, and quinazolines of Formula 1 above Another aspect of the present invention is to provide a method of inhibiting kinase activity in cancer cells. The method comprises the steps of:

1) providing a kinase inhibitor formulation comprising one or more quinolones, isoquinolines, and quinazolines, each of the quinolones, isoquinolines, and quinazolines including a N-phenylacetamide substituent and having an ortho substituent or an ortho and a para substituents relative to the N-phenylacetamide substituent; and 2) allowing the one or more quinolones, isoquinolines, and quinazolines to enter one or more of the cancer cells to thereby inhibit one or more kinases involved in one or more cell signaling pathways involved in cancer progression.

It is yet another aspect of the present invention to provide kinase inhibitor formulations that use modified forms or derivatives of one or more quinolones, isoquinolines, and quinazolines in accordance with Formula 1 that enhance uptake, enhance solubility, enhance efficacy, enhance retention, enhance pharmacokinetics, enhance selectivity, or reduce toxicity.

It is yet another aspect of the present invention that the modified forms and pharmaceutically acceptable derivatives of the one or more quinolones, isoquinolines, and quinazolines include derivatives of the one or more quinolones, isoquinolines, and quinazolines selected from the group comprising PEGylation products of the quinolones, isoquinolines, and quinazolines, protein-DNA complexes of the quinolones, isoquinolines, and quinazolines, protein conjugates of the quinolones, isoquinolines, and quinazolines, and combinations thereof.

It is yet another aspect of the present invention to provide a method of inhibiting kinase activity in cancer cells, wherein the one or more quinolones, isoquinolines, and quinazolines or the derivatives of the one or more quinolones, isoquinolines, and quinazolines are used in conjunction with a pharmaceutically acceptable carrier selected from the group consisting of micelles, liposomes, microspheres made of biodegradable polymer, albumin microspheres, synthetic polymer encapsulants, nanofibers, multifunctional inorganic nanoparticles, erythrocytes, virosomes, dendrimers, and combinations thereof.

It is yet another aspect of the present invention to provide a method of inhibiting kinase activity in cancer cells, wherein one or more quinolones, isoquinolines, and quinazolines according to Formula 1, their derivatives or combinations thereof are used as kinase inhibitors.

It is yet another aspect of the present invention to provide a formulation that contains quinolones, isoquinolines, and quinazolines that associate with the ATP binding pocket of wild type and T315I mutant of Bcr-Abl kinase.

It is yet another aspect of the present invention to provide a method of treating cancer in a mammal comprising the step of administering one or more quinolones, isoquinolines, and quinazolines and/or their derivatives, wherein the cancer being treated is a Bcr-Abl, STAT5, Crkl, Src kinases, or AMPK associated cancer, and wherein the one or more quinolones, isoquinolines, and quinazolines are administered by themselves or in combination with other kinase inhibitors.

It is yet another aspect of the present invention to provide a method of treating cancer in a mammal comprising the step of administering one or more quinolones, isoquinolines, and quinazolines, wherein the cancer being treated is chronic myeloid leukemia, acute myeloid leukemia, acute lymphoblastic leukemia or chronic lymphocytic leukemia.

It is yet another aspect of the present invention to provide a method of treating cancer cells comprising the step of treating the cancer cells with a formulation containing one or more quinolones, isoquinolines, and quinazolines and/or their derivatives, wherein the cancer cells have been treated with other kinase inhibitors.

It is yet another aspect of the present invention to provide a method of treating cancer cells comprising the step of treating the cancer cells with a formulation containing one or more quinolones, isoquinolines, and quinazolines and/or their derivatives, wherein the cancer cells have been treated with Imatinib.

It is yet another aspect of the present invention to provide a method of treating cancer in a mammalian subject comprising the step of administering a formulation containing one or more quinolones, isoquinolines, and quinazolines and/or their derivatives, wherein the cancer being treated is associated with Bcr-Abl, STAT5, Crkl, Src kinases, or AMPK and wherein the method is used to reduce an incidence or a relapse of the cancer in the subject by maintaining a low dose level of the kinase inhibitor formulation.

It is yet another aspect of the present invention to provide a method of treating cancer in a mammalian subject comprising the step of administering a formulation containing one or more quinolones, isoquinolines, and quinazolines and/or their derivatives, wherein the method is used for treating imatinib resistant mutations in subjects with chronic myeloid leukemia.

It is yet another aspect of the present invention to provide a method of treating cancer in a mammalian subject comprising the step of administering a formulation containing one or more quinolones, isoquinolines, and quinazolines and/or their derivatives, wherein the method is used for treating subjects with chronic myeloid leukemia treated with imatinib, dasatinib, nilotinib, or ponatinib (iclusig).

It is yet another aspect of the present invention to provide a method of treating cancer in a mammalian subject comprising the step of administering a formulation containing one or more quinolones, isoquinolines, and quinazolines and/or their derivatives, wherein the method is used for treatment of a subject such that the subject avoids the steroid dexamethasone or other steroids to overcome steroid induced side-effects.

It is yet another aspect of the present invention to provide a method of treating cancer in a mammalian subject comprising the step of administering a formulation containing one or more quinolones, isoquinolines, and quinazolines and/or their derivatives, wherein the treatment permits the subject to receive lower doses of steroids than in the currently used treatment methods to thereby reduce steroid-induced side effects.

It is yet another aspect of the present invention to provide a method of treating cancer in a mammalian subject comprising the step of administering a formulation containing one or more quinolones, isoquinolines, and quinazolines and/or their derivatives, wherein the methods leads to reduced incidences of steroid resistant cancer cells.

It is yet another aspect of the present invention to provide a method of treating cancer in a mammalian subject comprising the step of administering a formulation containing one or more quinolones, isoquinolines, and quinazolines and/or their derivatives, wherein the method is used to reduce the probability of relapse.

It is yet another aspect of the present invention to provide a method of treating cancer in a mammalian subject comprising the step of administering a formulation containing one or more quinolones, isoquinolines, and quinazolines and/or their derivatives, wherein the subject is treated with chemotherapeutic vincristine.

It is yet another aspect of the present invention to provide a method of treating cancer in a mammalian subject comprising the step of administering a formulation containing one or more quinolones, isoquinolines, and quinazolines and/or their derivatives, wherein the subject is treated with chemotherapeutic doxorubicin.

It is yet another aspect of the present invention to provide a method of treating cancer in a mammalian subject comprising the step of administering a formulation containing one or more quinolones, isoquinolines, and quinazolines and/or their derivatives, wherein the subject is treated with chemotherapeutic methotrexate.

It is yet another aspect of the present invention to provide a method of treating cancer in a mammalian subject comprising the step of administering a formulation containing one or more quinolones, isoquinolines, and quinazolines and/or their derivatives, wherein the subject is treated with a combination of chemotherapeutics vincristine, doxorubicin and methotrexate.

It is yet another aspect of the present invention to provide a method of using quinolones, isoquinolines, and quinazolines and/or their related analogs to treat leukemia.

It is yet another aspect of the present invention to provide a method of using quinolones, isoquinolines, and quinazolines and/or related molecules as drugs for Gleevec resistant chronic myeloid leukemia.

It is yet another aspect of the present invention to provide a method of using quinolones, isoquinolines, and quinazolines and/or related molecules as potential drugs for acute lymphoid leukemia.

It is yet another aspect of the present invention to provide a method of using quinolones, isoquinolines, and quinazolines and/or related molecules as drugs for acute myeloid leukemia.

It is yet another aspect of the present invention to provide a method of using quinolones, isoquinolines, and quinazolines and/or related molecules as drugs for chronic lymphoid leukemia.

It is yet another aspect of the present invention to provide a method of using quinolones, isoquinolines, and quinazolines and/or related molecules as inhibitors of Bcr-Abl kinase.

It is yet another aspect of the present invention to provide a method of using quinolones, isoquinolines, and quinazolines and/or related molecules as Src inhibitors.

It is yet another aspect of the present invention to provide a method of using quinolones, isoquinolines, and quinazolines and/or related molecules as drugs for treatment of cancer involving activation of Src and/or Bcr-Abl kinases.

It is an aspect of the present invention to provide a formulation for inhibiting kinase activity in cancer cells, such as for example leukemic cells, wherein the formulation comprises a first component selected from the group consisting of dioxinoquinolines having a N-phenylacetamide substituent and also having an ortho substituent or an ortho and a para substituents relative to the N-phenylacetamide substituent, their derivatives, and combinations thereof, and a second component comprising, for example, a pharmaceutically acceptable carrier, delivery vehicle, or excipient.

It is another aspect of the present invention to provide a formulation wherein the derivatives are selected from the group consisting of PEGylation products of the dioxinoquinolines, protein-DNA complexes of the dioxinoquinolines, protein conjugates of the dioxinoquinolines, prodrugs of the dioxinoquinolines, any compound that yields the inhibitors of the present invention or their derivatives as a metabolite in living cells or in a living organism and combinations thereof.

It is yet another aspect of the present invention to provide a formulation including the dioxinoquinolines and/or their derivatives and further comprising a pharmaceutically acceptable carrier selected from the group consisting of micelles, liposomes, microspheres made of biodegradable polymer, albumin microspheres, synthetic polymer encapsulants, nanofibers, multifunctional inorganic nanoparticles, erythrocytes, virosomes, dendrimers, and combinations thereof.

It is still another aspect of the present invention to provide a kinase inhibitor formulation including the dioxinoquinolines of Formula 2 above Another aspect of the present invention is to provide a method of inhibiting kinase activity in cancer cells. The method comprises the steps of:

1) providing a kinase inhibitor formulation comprising one or more dioxinoquinolines, each of the dioxinoquinolines including a N-phenylacetamide substituent and having an ortho substituent or an ortho and a para substituents relative to the N-phenylacetamide substituent; and 2) allowing the one or more dioxinoquinolines to enter one or more of the cancer cells to thereby inhibit one or more kinases involved in one or more cell signaling pathways involved in cancer progression.

It is yet another aspect of the present invention to provide kinase inhibitor formulations that use modified forms or derivatives of one or more dioxinoquinolines in accordance with Formula 2 that enhance uptake, enhance solubility, enhance efficacy, enhance retention, enhance pharmacokinetics, enhance selectivity, or reduce toxicity.

It is yet another aspect of the present invention that the modified forms and pharmaceutically acceptable derivatives of the one or more dioxinoquinolines include derivatives of the one or more dioxinoquinolines selected from the group comprising PEGylation products of the dioxinoquinolines, protein-DNA complexes of the dioxinoquinolines, protein conjugates of the dioxinoquinolines, and combinations thereof.

It is yet another aspect of the present invention to provide a method of inhibiting kinase activity in cancer cells, wherein the one or more dioxinoquinolines or the derivatives of the one or more dioxinoquinolines are used in conjunction with a pharmaceutically acceptable carrier selected from the group consisting of micelles, liposomes, microspheres made of biodegradable polymer, albumin microspheres, synthetic polymer encapsulants, nanofibers, multifunctional inorganic nanoparticles, erythrocytes, virosomes, dendrimers, and combinations thereof.

It is yet another aspect of the present invention to provide a method of inhibiting kinase activity in cancer cells, wherein one or more dioxinoquinolines according to Formula 2, their derivatives or combinations thereof are used as kinase inhibitors.

It is yet another aspect of the present invention to provide a formulation that has an inhibitory action on Bcr-Abl kinase.

It is yet another aspect of the present invention to provide a formulation that has an inhibitory action on the mutated form of Bcr-Abl kinase resulting from the T315I mutation of Bcr-Abl.

It is yet another aspect of the present invention to provide a formulation that contains dioxinoquinolines that associate with the ATP binding pocket of wild type and T315I mutant of Bcr-Abl kinase.

It is yet another aspect of the present invention to provide a formulation that has an inhibitory action on the phosphorylation of STAT5 and its downstream target Crkl.

It is yet another aspect of the present invention to provide a formulation that has an inhibitory action on the phosphorylation of Src family kinases selected from the group consisting of Src, Lyn, Yes, LCK, HCK, and combinations thereof.

It is yet another aspect of the present invention to provide a formulation that has an inhibitory action on the phosphorylation of AMPK.

It is yet another aspect of the present invention to provide a method of treating cancer in a mammal comprising the step of administering one or more dioxinoquinolines and/or their derivatives, wherein the cancer being treated is a Bcr-Abl, STAT5, Src kinases, or AMPK associated cancer, and wherein the one or more dioxinoquinolines are administered by themselves or in combination with other kinase inhibitors.

It is yet another aspect of the present invention to provide a method of treating cancer in a mammal comprising the step of administering one or more dioxinoquinolines, wherein the cancer being treated is chronic myeloid leukemia, acute myeloid leukemia, acute lymphoblastic leukemia or chronic lymphocytic leukemia.

It is yet another aspect of the present invention to provide a method of treating cancer cells comprising the step of treating the cancer cells with a formulation containing one or more dioxinoquinolines and/or their derivatives, wherein the cancer cells have been treated with other kinase inhibitors.

It is yet another aspect of the present invention to provide a method of treating cancer cells comprising the step of treating the cancer cells with a formulation containing one or more dioxinoquinolines and/or their derivatives, wherein the cancer cells have been treated with Imatinib.

It is yet another aspect of the present invention to provide a method of treating cancer in a mammalian subject comprising the step of administering a formulation containing one or more dioxinoquinolines and/or their derivatives, wherein the cancer being treated is associated with Bcr-Abl, STAT5, Src kinases, or AMPK and wherein the method is used to reduce an incidence or a relapse of the cancer in the subject by maintaining a low dose level of the kinase inhibitor formulation.

It is yet another aspect of the present invention to provide a method of treating cancer in a mammalian subject comprising the step of administering a formulation containing one or more dioxinoquinolines and/or their derivatives, wherein the method is used for treating imatinib resistant mutations in subjects with chronic myeloid leukemia.

It is yet another aspect of the present invention to provide a method of treating cancer in a mammalian subject comprising the step of administering a formulation containing one or more dioxinoquinolines and/or their derivatives, wherein the method is used for treating subjects with chronic myeloid leukemia treated with imatinib, dasatinib, nilotinib, or ponatinib (iclusig).

It is yet another aspect of the present invention to provide a method of treating cancer in a mammalian subject comprising the step of administering a formulation containing one or more dioxinoquinolines and/or their derivatives, wherein the method is used for treatment of a subject such that the subject avoids the steroid dexamethasone or other steroids to overcome steroid induced side-effects.

It is yet another aspect of the present invention to provide a method of treating cancer in a mammalian subject comprising the step of administering a formulation containing one or more dioxinoquinolines and/or their derivatives, wherein the treatment permits the subject to receive lower doses of steroids than in the currently used treatment methods to thereby reduce steroid-induced side effects.

It is yet another aspect of the present invention to provide a method of treating cancer in a mammalian subject comprising the step of administering a formulation containing one or more dioxinoquinolines and/or their derivatives, wherein the methods leads to reduced incidences of steroid resistant cancer cells.

It is yet another aspect of the present invention to provide a method of treating cancer in a mammalian subject comprising the step of administering a formulation containing one or more dioxinoquinolines and/or their derivatives, wherein the method is used to reduce the probability of relapse.

It is yet another aspect of the present invention to provide a method of treating cancer in a mammalian subject comprising the step of administering a formulation containing one or more dioxinoquinolines and/or their derivatives, wherein the subject is treated with chemotherapeutic vincristine.

It is yet another aspect of the present invention to provide a method of treating cancer in a mammalian subject comprising the step of administering a formulation containing one or more dioxinoquinolines and/or their derivatives, wherein the subject is treated with chemotherapeutic doxorubicin.

It is yet another aspect of the present invention to provide a method of treating cancer in a mammalian subject comprising the step of administering a formulation containing one or more dioxinoquinolines and/or their derivatives, wherein the subject is treated with chemotherapeutic methotrexate.

It is yet another aspect of the present invention to provide a method of treating cancer in a mammalian subject comprising the step of administering a formulation containing one or more dioxinoquinolines and/or their derivatives, wherein the subject is treated with a combination of chemotherapeutics vincristine, doxorubicin and methotrexate.

It is yet another aspect of the present invention to provide a method of using dioxinoquinolines and/or their related analogs to treat leukemia.

It is yet another aspect of the present invention to provide a method of using dioxinoquinolines and/or related molecules as drugs for Gleevec resistant chronic myeloid leukemia.

It is yet another aspect of the present invention to provide a method of using dioxinoquinolines and/or related molecules as potential drugs for acute lymphoid leukemia.

It is yet another aspect of the present invention to provide a method of using dioxinoquinolines and/or related molecules as drugs for acute myeloid leukemia.

It is yet another aspect of the present invention to provide a method of using dioxinoquinolines and/or related molecules as drugs for chronic lymphoid leukemia.

It is yet another aspect of the present invention to provide a method of using dioxinoquinolines and/or related molecules as inhibitors of Bcr-Abl kinase.

It is yet another aspect of the present invention to provide a method of using dioxinoquinolines and/or related molecules as Src inhibitors.

It is yet another aspect of the present invention to provide a method of using dioxinoquinolines and/or related molecules as drugs for treatment of cancer involving activation of Src and/or Bcr-Abl kinases.

It is yet another aspect of the present invention to provide a method of treating cancer cells in a subject using a formulation according to the present invention wherein the subject is also treated with microtubule function affecting chemotherapeutic agents such as vincristine, vinblastine and taxotere.

It is yet another aspect of the present invention to provide a method of treating cancer cells in a subject using a formulation according to the present invention wherein the subject is treated with alkylating chemotherapeutic agents such as cyclophosphamide and cisplatin.

It is yet another aspect of the present invention to provide a method of treating cancer cells in a subject using a formulation according to the present invention wherein the subject is treated with anthracycline chemotherapeutic agents such as doxorubicin and daunorubicin.

It is yet another aspect of the present invention to provide a method of treating cancer cells in a subject using a formulation according to the present invention wherein the subject is treated with antifolate chemotherapeutic methotrexate.

It is yet another aspect of the present invention to provide a method of treating cancer cells in a subject using a formulation according to the present invention wherein the subject is treated with a combination of chemotherapeutics, steroids, microtubule inhibitors, alkylating agents, anthracyclines and antifolates.

It is yet another aspect of the present invention to provide a method of treating a subject using a formulation according to the present invention wherein the subject is treated with steroids or antifolates for arthritis.

It is yet another aspect of the present invention to provide a method of treating a subject using a formulation according to the present invention wherein the subject is treated with steroids or antifolates for connective tissue disorders.

It is yet another aspect of the present invention to provide a method of treating acute or chronic inflammation in a subject using a formulation according to the present invention wherein the subject is treated with steroids.

It is yet another aspect of the present invention to provide a method of inhibiting kinase activity in cancer cells, the method comprising the steps of providing a kinase inhibitor formulation in accordance with the present invention; and allowing the kinase inhibitor formulation to enter one or more of the cancer cells to thereby inhibit one or more kinases involved in one or more cell signaling pathways involved in progression of cancer or inflammatory conditions.

It is yet another aspect of the present invention to provide a kinase inhibitor formulation according to the present invention wherein said vehicle comprises starch.

It is yet another aspect of the present invention to provide a kinase inhibitor formulation according to the present invention wherein said vehicle comprises water. It is yet another aspect of the present invention to provide a kinase inhibitor formulation according to the present invention wherein said vehicle comprises glycerin.

It is yet another aspect of the present invention to provide a kinase inhibitor formulation including a first component selected from the compounds according to formula 2, their derivatives, and mixtures thereof, wherein R3 is $CH_3$.

It is yet another aspect of the present invention to provide a kinase inhibitor formulation including a first component selected from the compounds according to formula 2, their derivatives, and mixtures thereof, wherein R1 is COO—$CH_3$, and wherein R2 is H.

It is yet another aspect of the present invention to provide a kinase inhibitor formulation including a first component selected from the compounds according to formula 2, their derivatives, and mixtures thereof, wherein R1 is H, and wherein R2 is F.

It is yet another aspect of the present invention to provide a kinase inhibitor formulation including a first component selected from the compounds according to formula 2, their derivatives, and mixtures thereof, wherein R3 is $CH_2$—$CH_3$.

It is yet another aspect of the present invention to provide a kinase inhibitor formulation including a first component selected from the compounds according to formula 2, their derivatives, and mixtures thereof, wherein R1 is O—$CH_3$, and wherein R2 is O—$CH_3$.

It is yet another aspect of the present invention to provide a kinase inhibitor formulation including a first component selected from the compounds according to formula 2, their derivatives, and mixtures thereof, wherein R1 is H, and wherein R2 is $CH_3$.

It is yet another aspect of the present invention to provide a kinase inhibitor formulation including a first component selected from the compounds according to formula 2, their derivatives, and mixtures thereof, wherein R1 is O—$CH_3$, and wherein R2 is H.

It is yet another aspect of the present invention to provide a kinase inhibitor formulation including a first component selected from the compounds according to formula 2, their derivatives, and mixtures thereof, wherein R1 is H and wherein R2 is O—$CH_3$.

It is yet another aspect of the present invention to provide a kinase inhibitor formulation including a first component selected from the compounds according to formula 2, their derivatives, and mixtures thereof, wherein R3 is C≡N.

It is yet another aspect of the present invention to provide a kinase inhibitor formulation including a first component selected from the compounds according to formula 2, their derivatives, and mixtures thereof, wherein R1 is O—$CH_3$, and wherein R2 is H.

These and other objects of the present invention will become apparent from the attached description and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 shows the inhibitory effect of compounds according to the present invention on the phosphorylation of STAT5.

FIG. 8 shows the inhibitory effect of compounds according to the present invention on the phosphorylation of Crkl.

FIGS. 9-10 show the inhibitory effect of compounds according to the present invention on the phosphorylation of Src.

DETAILED DESCRIPTION OF THE PREFERRED EMBODIMENTS

Figure 1:
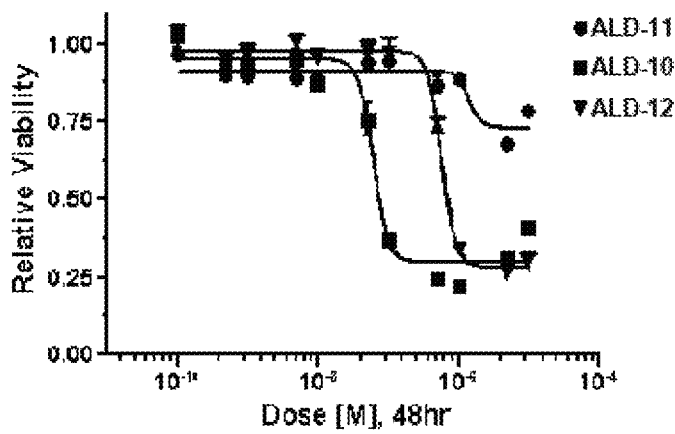
FIG. 1 is a graph showing the effect of compounds according to the present invention on the viability of Gleevec resistant K562 cells.

The present invention is directed to small molecules that show significant cytotoxicity in leukemic cells derived from acute lymphoid leukemia (ALL), acute myeloid leukemia (AML), chronic myeloid leukemia (CML), and chronic lymphoid leukemia (CLL). One such compound is designated herein as anti-leukemia drug 4 (ALD-4). This compound is highly cytotoxic to Gleevec resistant CML (GRCML). Structure of ALD-4 is shown below. There are about 122 analogs of this compound. Initial analysis of the cytotoxicity of 12 of these compounds, including ALD-4, (designated ALD-1 through ALD-12 herein) revealed that those designated ALD-1, ALD-9 and ALD-11 were non-toxic to the leukemic cells tested, whereas those designated ALD-4, ALD-10, and ALD-12 were toxic to the leukemic cells. The compound ALD-4 is commercially available from Asinex, as are 122 of its analogs, which are closely related compounds with the same ring structure and thio-amide linker.

Materials and Methods:

The Chemical name for ALD-1 is 4-[2-(8-Methyl-2,3-dihydro-[1,4]dioxino[2,3-g]quinolin-7-ylsulfanyl)-acetylamino]-benzoic acid methyl ester and it has the following structure:

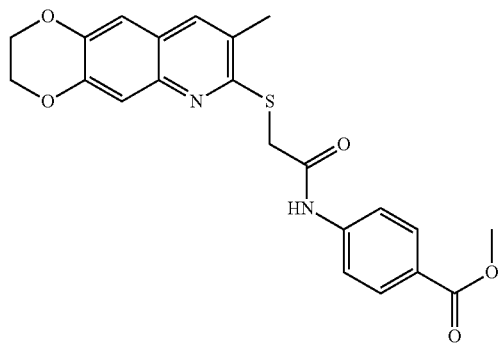 [SMILES: COC(=O)c1ccc(NC(=O)CSc2nc3cc4c(cc3cc2C)OCCO4)cc1]

ALD-1 has the molecular formula $C_{22}H_{20}N_2O_5S$ and a molecular weight of 424.475 g/mole. The designation of the manufacturer Asinex for this compound is ASN 04371279.

The Chemical name for ALD-4 is N-(2,4-Dimethoxy-phenyl)-2-(8-ethyl-2,3-dihydro-[1,4]dioxino[2,3-g]quinolin-7-ylsulfanyl)-acetamide and it has the following structure:

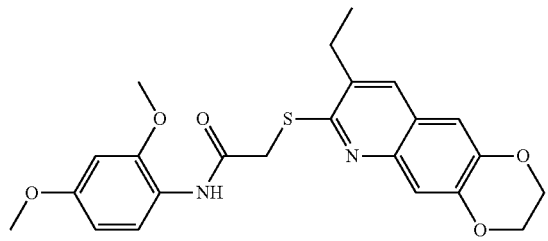 [SMILES: CCc1cc2cc3c(cc2nc1SCC(=O)Nc1ccc(OC)cc1OC)OCCO3]

ALD-4 has the molecular formula $C_{23}H_{24}N_2O_5S$ and a molecular weight of 440.5176 g/mole. The designation of the manufacturer Asinex for this compound is ASN 05548624.

The Chemical name for ALD-6 is 2-(8-Cyano-2,3-dihydro-[1,4]dioxino[2,3-g]quinolin-7-ylsulfanyl)-N-(4-methoxy-phenyl)-acetamide and it has the following structure:

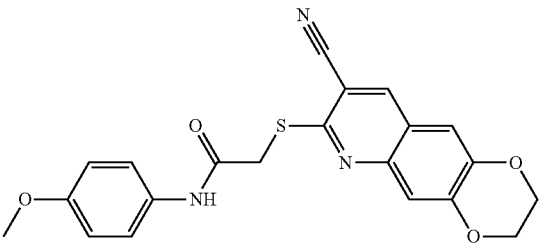 [SMILES: COc1ccc(NC(=O)CSc2nc3cc4c(cc3cc2C#N)OCCO4)cc1]

ALD-6 has the molecular formula $C_{21}H_{17}N_3O_4S$ and a molecular weight of 407.4483 g/mole. The designation of the manufacturer Asinex for this compound is ASN 05588690.

ALD-9, 2-(8-Ethyl-2,3-dihydro-[1,4]dioxino[2,3-g]quinolin-7-ylsulfanyl)-N-(2-fluoro-phenyl)-acetamide, has the following structure:

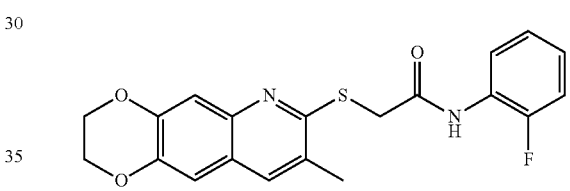

ALD-9 has the molecular formula $C_{21}H_{19}F N_2O_3S$ and a molecular weight of 398.4561 g/mole. The designation of the manufacturer Asinex for this compound is ASN 05548667.

ALD-10, 2-(8-Ethyl-2,3-dihydro-[1,4]dioxino[2,3-g]quinolin-7-ylsulfanyl)-N-o-tolyl-acetamide, has the following structure:

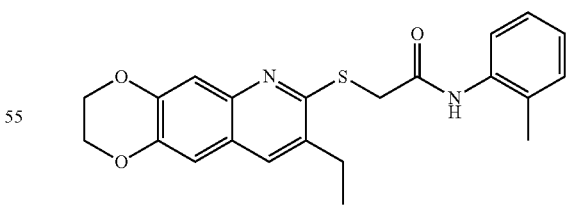

ALD-10 has the molecular formula $C_{22}H_{22}N_2O_3S$ and a molecular weight of 394.4928 g/mole. The designation of the manufacturer Asinex for this compound is ASN 05548609.

ALD-11, 2-(8-Ethyl-2,3-dihydro-[1,4]dioxino[2,3-g]quinolin-7-ylsulfanyl)-N-(4-methoxy-phenyl)-acetamide, has the following structure:

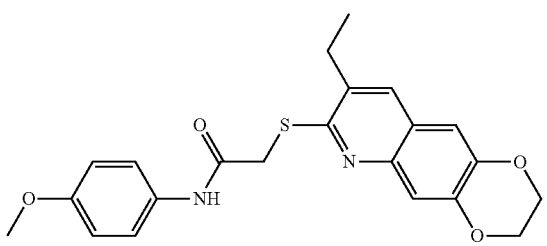 [SMILES: CCc1cc2cc3c(cc2nc1SCC(=O)Nc1ccc(OC)cc1)OCCO3]

ALD-11 has the molecular formula $C_{22}H_{22}N_2O_4S$ and a molecular weight of 410.4918 g/mole. The designation of the manufacturer Asinex for this compound is ASN 05548619.

ALD-12, 2-(8-ethyl-2,3-dihydro-[1,4]dioxino[2,3-g]quinolin-7-ylsulfanyl)-N-(2-methoxy-phenyl)-acetamide, has the following structure:

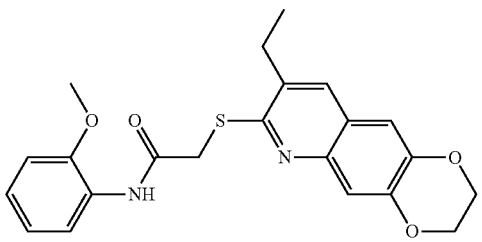 [SMILES: CCc1cc2cc3c(cc2nc1SCC(=O)Nc1ccccc1OC)OCCO3]

ALD-12 has the molecular formula $C_{22}H_{22}N_2O_4S$ and a molecular weight of 410.4918 g/mole. The designation of the manufacturer Asinex for this compound is ASN 05548708.

Hela (established from epithelioid cervical carcinoma), were purchased from the American Type Culture Collection (ATCC, Manassas, Va.). SN12C and ACHN cells were provided by Dr. Charles Sawyers. Hela, SN12C and ACHN cells were maintained in DMEM media (Life Technologies) supplemented with 10% FBS, glutamine and penicillin/streptomycin Gleevec resistant K562 cells were provided by Dr. Bruno Calabratta, Thomas Jefferson University. Normal lymphocyte 9093 was purchased from ATCC. K562 and normal lymphocytes were maintained in RPMI media (Life Technologies) supplemented with 20% fetal bovine serum (FBS). K562 cells were maintained in the 1 µM Gleevec. All cells were maintained at 37° C. under a humidified atmosphere of 95% air and 5% $CO_2$.

Cytotoxicity:

The cells were seeded at an initial density of 50,000 cells per well in 100 µl of cell culture media constituted with or without drugs at increasing doses ranging from 1 to $10^7$ fold. The assays were performed in 96-well cell culture plates which were maintained at 37° C. in 5% $CO_2$ atmosphere for 24 h, 48 h, 72 h and 96 h. At the end of each incubation point; cell viability was measured by Cell Titer-Blue® Assay. The measurements were then expressed as the percentage of viable cells compared to the survival of respective control groups (untreated cells) defined as the maximum cell viability. The data obtained was further analyzed using Prism nonlinear regression software (Graphpad Software) for the curve-fitting and determination of IC50 values.

Western Blotting:

K562 cells were plated in 10 cm dishes at densities of $5×10^6$ cells/dish and incubated with or without drugs at multiple doses of ALDs. Post incubation, the cells were collected, washed with cold PBS twice and centrifuged at 2000 rpm for 5 min. The cell pellets obtained were resuspended in a lysis buffer (20 mM Tris-HCL, pH 7.5; 150 mM Sodium Chloride; 1 mM EDTA; 1 mM EGTA; 1 mM β-Glycerol Phosphate; 1 mM Sodium Vanadate; 1.25 mM Sodium Pyrophosphate; 1% (w/v) Triton X-100) and protease inhibitor cocktail (100 mM Phenylmethylsulfonyl Fluoride, 1:100; 15 mg/ml mixture of Antipain, Leupeptin, Pepstatin, 1:1000; Sigma-Aldrich St Louis, Mo.) at 4° C. for 1 h. The cell lysates were prepared from the homogenates by sonication and centrifugation at 12,000 rpm and 4° C. for 15 min. The concentration of protein in the lysates was estimated using a protein assay kit (DC protein assay reagent, Bio-Rad, Hercules, Calif., USA). Equal amounts of protein (30-50 µg) were resolved on 10% SDS-PAGE gels and transferred overnight onto nitrocellulose membranes (Bio-Rad) in 20% methanol, 25 mM Tris, and 192 mM glycine. After transfer, the membranes were blotted with a rabbit polyclonal to active+pro caspase-3 antibody (1:1000, Abcam, Cambridge, Mass.) and a mouse monoclonal antibody to tubulin (1:10000, Abcam, Cambridge, Mass.) and visualized by Enhanced Chemiluminescence Plus reagent (GE Healthcare, Piscataway, N.J.) followed by exposure to X-ray film (Amersham Biosciences, Piscataway, N.J.).

Computer Modeling:

Computer simulations were carried out to determine the binding affinity of ALD 10 in the ATP binding pocket of wild type and T315I mutant Bcr-Abl kinase in comparison to Gleevec. The results of the computer simulations are presented below and in FIGS. 12(a) through 12(d).

Results and Discussion:

Structure of the ALDs:

The structures of some of the ALDs tested, including those discussed below, are shown above. The compounds described below fall within the Formulas 1 and 2. The ALD-4, ALD-10 and ALD-12 show anti-leukemic activity whereas the ALD-11 is inactive. The structure-activity relationship reveals that an ortho substituent (as in ALD-10 and ALD-12) or ortho and para substituents (as in ALD-4) relative to the N-phenylacetamide substituent of the compound exhibit higher levels of kinase inhibitor activity. A compound with a para substituent alone (as in ALD-11) appears to be inactive.

ALDs Induce Cytotoxicity in Gleevec Resistant CML Cells:

FIG. 1 shows induction of cytotoxicity by ALD-10 and ALD-12 but not by ALD-11 in Gleevec resistant K562 cells. The well-established CML cell line K562 which is Gleevec-resistant and grows normally in the presence of 1 µM of Gleevec was used to test the cytotoxicity of the ALD compounds according to the present invention. Referring to FIG. 1, the ALD-11 was not cytotoxic whereas ALD-10 and ALD-12 were cytotoxic and showed an IC50 value of 0.0746 µM and 0.0697 µM, respectively.

Figure 2A:
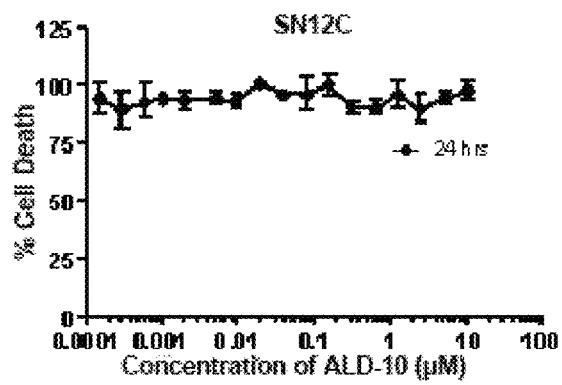
FIGS. 2A-2B are graphs showing the effect of a compound according to the present invention on cultured kidney carcinoma cells SN12C and ACHN.
Figure 2B:
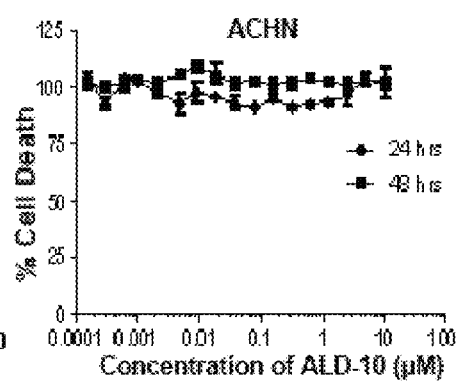
Figure 3A:
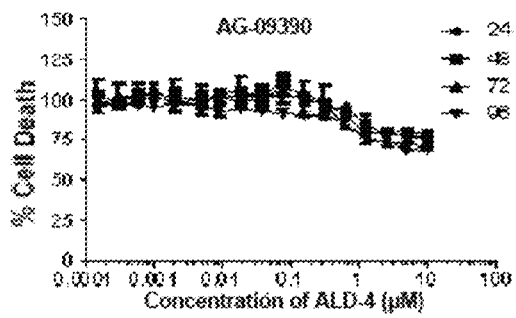
FIGS. 3A-3B are graphs showing the effect of a compound according to the present invention on transformed normal lymphocytes.
Figure 3B:
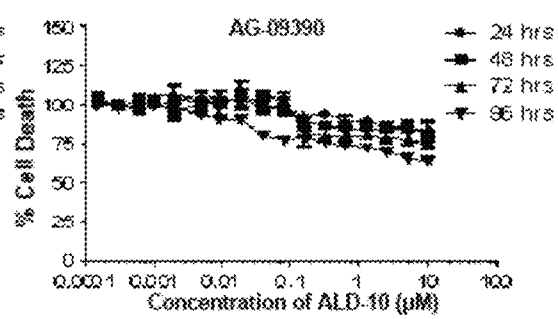

FIGS. 2A and 2B show that ALD compounds were non-toxic to renal cell carcinoma cell lines. FIGS. 3A and 3B show minimal toxicity of ALD compounds on transformed normal lymphocytes.

ALD compounds showed no toxicity in cultured kidney carcinoma cells such as SN12C and ACHN (see FIGS. 2A and 2B). In addition, immortalized normal lymphocytes showed less cytotoxicity compared to K562 cells (see FIGS. 3A and 3B). The effects of ALDs on Gleevec-resistant CML lines such as LAMAR and KCL22 cell lines were tested and were found to be cytotoxic to these cell lines as well. These results suggest that ALD compounds are significantly toxic to Gleevec-resistant CML cells.

Figure 4:
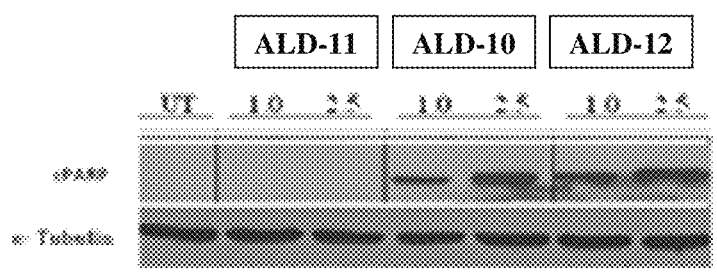
FIG. 4 shows the effect of compounds according to the present invention in terms of the induction of apoptotic cell death in Gleevec-resistant CML cell lines as visualized by PARP cleavage, which is a marker for apoptotic cell death.

FIG. 4 shows induction of PARP cleavage by ALD-10 and ALD-12 but not by ALD-11. In the figures UT stands for untreated.

Referring to FIG. 4, ALDs of the present invention induce apoptotic cell death in Gleevec-resistant CML lines as visualized by the cleavage of an apoptosis marker PARP. Interestingly, ALD-11 did not reveal PARP cleavage indicating that this analog is inactive in inducing apoptotic cell death in CML cells which correlates with the observed lack of cytotoxicity of this analog.

Figures 5, 6:
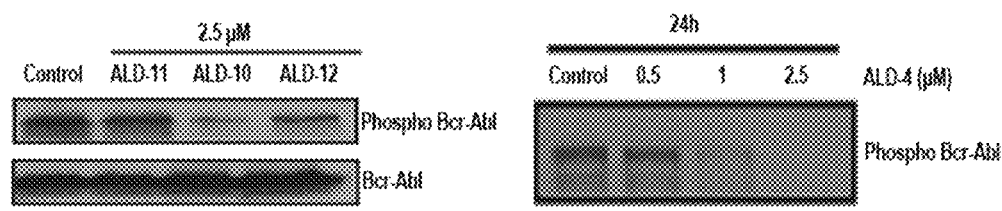
FIGS. 5-6 show the inhibitory effect of compounds according to the present invention on the phosphorylation of Bcr-Abl.

ALDs Inhibit Bcr-Abl Phosphorylation:

FIGS. 5 and 6 show that ALD-4, ALD-10 and ALD-12 block phosphorylation of Bcr-Abl Kinase. The bottom panel in FIG. 5 shows total protein levels of Bcr-Abl. Bcr-Abl fusion gene product is activated by phosphorylation in CML cells. Gleevec associates with the ATP binding pocket of the Bcr-Abl and inhibits its phosphorylation. T315I mutation of the Bcr-Abl prevents Gleevec binding to this protein and therefore this mutant Bcr-Abl remains active in CML cells, imparting resistance to Gleevec. Interestingly, ALDs inhibit Bcr-Abl in the presence of Gleevec in K562 cells that express the T315I mutant Bcr-Abl (see FIGS. 5 and 6). It is possible that ALDs bind to the ATP binding pocket of the mutated protein (see FIGS. 12(c) and 12(d)). Also, it is possible that ALDs may bind to one or multiple 3-dimensional pockets in the mutant Bcr-Abl. This binding might induce a conformational change that inhibits its phosphorylation and thus leads to the subsequent inactivation of Bcr-Abl.

ALDs Inhibit (Signal Transducer and Activator of Transcription) Protein (STAT5) and Crkl Phosphorylation:

FIGS. 7 and 8 show that ALD-10 and ALD-12 inhibited STAT5 and CrkL phosphorylation. The bottom panels represent total level of STAT5 and Crkl. Note that the ALD-11 did not affect the phosphorylation of STAT5 or Crkl. Treatment of K562 cells with ALD-10 and ALD-12 significantly reduced the phosphorylation of STAT5 and the adaptor protein Crkl (see FIGS. 7 and 8). This result indicates that inhibition of BCR-Abl phosphorylation is associated with attenuation of activation of its downstream activators STAT5 and Crkl.

Figure 11:
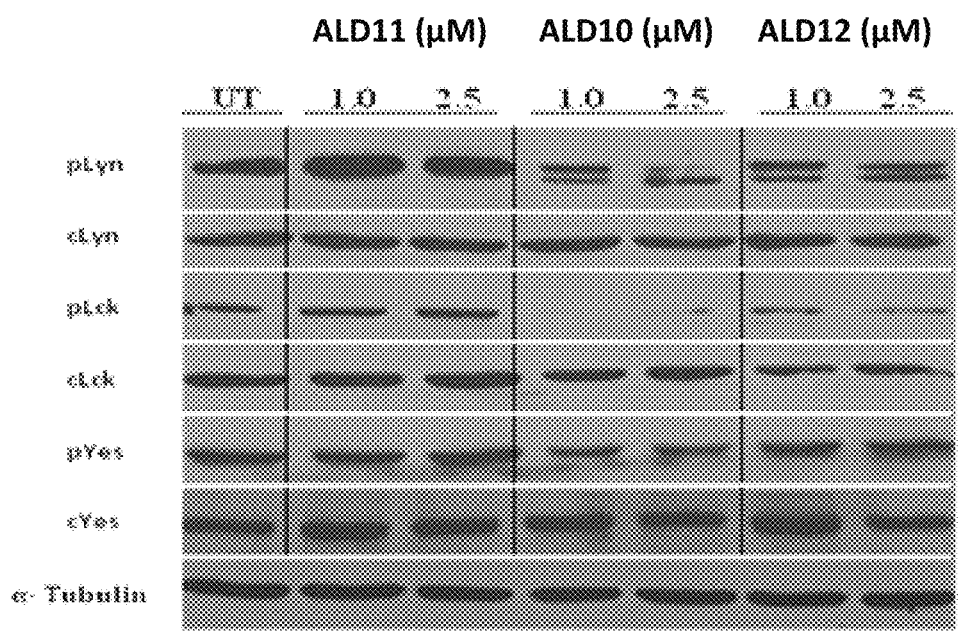
FIG. 11 shows the inhibitory effect of compounds according to the present invention on the phosphorylation of Lyn, LCK and Yes.

ALDs Inhibit Src Kinase Phosphorylation:

FIG. 9 shows that phosphorylation of Src was inhibited by ALD-4. FIG. 10 shows that phosphorylation of Src was inhibited by ALD-10 and ALD-12. Note that ALD-11 did not affect Src phosphorylation. FIG. 11 shows the Inhibition of phosphorylation of Lyn, LCK and Yes by ALD-10 and ALD-12.

ALD-4, ALD-10 and ALD-12 reduced the levels of phosphorylated Src in K562 cells whereas ALD-11 did not show any effect (see FIGS. 9 and 10). Of the five Src kinases, Lyn, Lck and Yes were significantly inhibited by ALD-10 and ALD-12 but not by ALD-11 (See FIG. 11). Src is also known to phosphorylate STAT5 and activate its transcription. It is possible that ALDs reduce phosphorylation of BCR-Abl which in turn inhibits Src kinases phosphorylation and its downstream effects. It is also possible that ALDs inhibit Src kinases independent of BCR-Abl. These data suggest that ALDs are like double-edged swords and have the potential to inhibit both Src and BCR-Abl kinases which are key enzymes involved CML leukemogenesis and maintenance.

Figure 12:
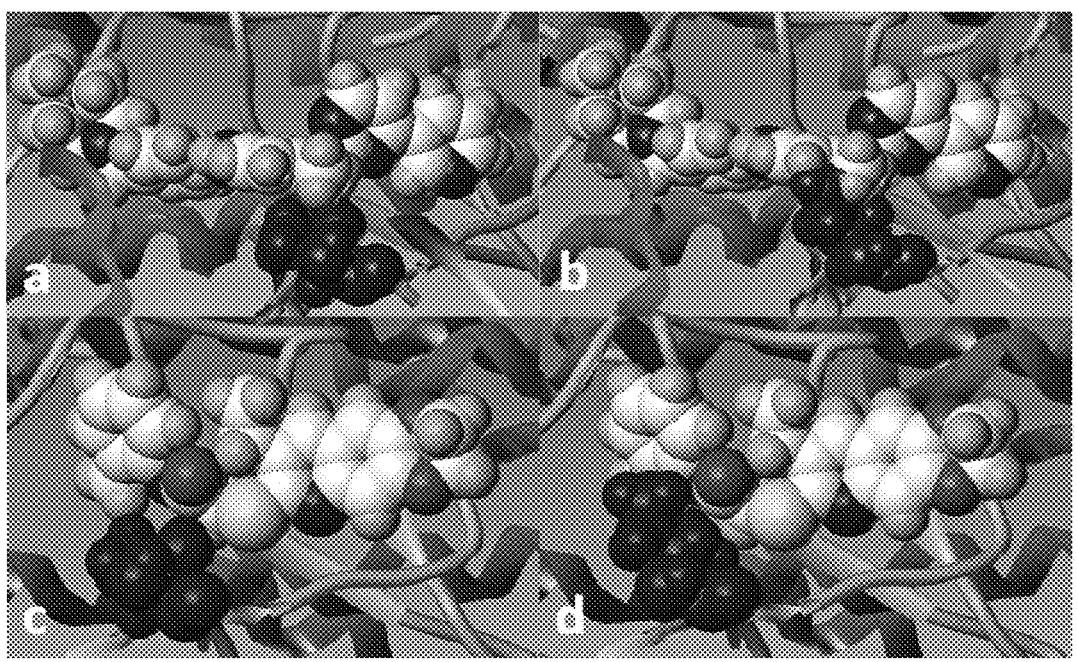
FIG. 12 (*a*) through (*d*) show computer modeling results revealing the binding of ALD 10 in the ATP binding pocket of wild type and T315I mutant Bcr-Abl kinase in comparison to Gleevec.

ALD Binds to the ATP Binding Pocket of T315I Mutant Bcr-Abl Kinase:

FIGS. 12(a) and 12(b) show the binding of Gleevec to Bcr-Abl ATP binding pocket of native (i.e. wild type) and T315I mutant Bcr-Abl, respectively. Note that Gleevec does not associate with the mutant protein. FIGS. 12(c) and 12(d) show the binding of ALD10 to native and mutant Bcr-Abl protein, respectively. The binding affinities of Gleevec and ALD-10 for the ATP binding pocket of the native and mutant Bcr-Abl protein, as determined by the computer simulation studies, are shown in Table 1 below.

TABLE 1

| Compound | Docking Score |
| --- | --- |
| Gleevec in wild type Bcr-Abl | 10.14 |
| ALD-10 in wild type Bcr-Abl | 7.74 |
| ALD-10 in T315I | 8.27 |

Note that a steric clash occurs with the mutant Abl only for Gleevec, and ALD-10 fits perfectly in the binding site. The images in FIGS. 12(a) through 12(b) were rendered with the SYBYL molecular modeling program. The docking scores in wild type and mutant Bcr-Abl were calculated using the Surflex program. Note that Gleevec fails to bind to the T315I mutant Bcr-Abl protein, so a docking score cannot be provided.

Figure 13:
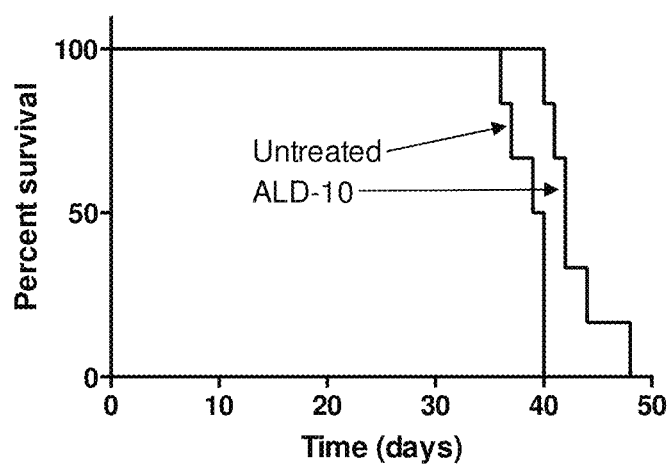
FIG. 13 shows the results of a mouse study using a kinase inhibitor of the present invention.

Preclinical Efficacy Evaluation:

Referring to FIG. 13, a preclinical study was performed in mice using a kinase inhibitor according to the present invention.

BV173-GFP, a Gleevec resistant chronic myeloid leukemic cells expressing green fluorescent protein, ($1 \times 10^6$) were injected via the tail vein into female NSG-B2m mice (6-8 weeks old; 6 per group). Two days after leukemia cell injection, the mice received intraperitoneal treatments of DMSO, or ALD-10 in DMSO. Following injection cells, the mice were randomized into two groups (6/group) to receive DMSO, or ALD-10. The mice received up to 250 mg/kg of ALD10 for 5 weeks. Kaplan-Meier survival curves showed that mice that received ALD-10 survived longer (48 days compared to 40 days of DMSO treated). The median survival for ALD-10 and DMSO treated mice was 42 and 39 days, respectively. The improved survival in ALD 10 treated mice showed excellent statistical significance by two different tests: Log-rank (Mantel-Cox) test (P value=statistically significant (P value=0.0036 and Gehan-Breslow-Wilcoxon test (P value=0.0045). A p<0.05 was considered significant. Moreover, the group that received ALD-10 were considerably more active and showed reduced liver tumor mass compared to DMSO treated mice. The preclinical study was performed according to Institutional Animal Care and Use Committee (IACUC) guidelines at the University of Delaware Animal facility with approval from the University IACUC committee.

Taken together the results reveal that ALDs have strong cytotoxic activity on Gleevec resistant CML cells in vitro and in vivo have the potential as therapeutics for Gleevec-resistant CML in adults. Since these drugs have anti-leukemia activity on acute lymphoid and acute myeloid leukemia these drugs will also have therapeutic potential to treat acute lymphoid leukemia and acute myeloid leukemia in children and adults.

Delivery vehicles, carriers, adducts, adjuvants, additives, excipients, diluents, solvents, dosage forms, and treatment protocols suitable for use in the present invention can be found in U.S. Pat. Nos. 8,114,874, 8,293,756, 7,153,856, 7,125,875, and 6,596,746, which are incorporated herein by reference.

In general, the present invention is directed to a composition comprising a kinase inhibitor selected from the group consisting of quinolones, isoquinolines, quinazolines, their modifications and derivatives, and combinations thereof, and a pharmaceutically acceptable vehicle. "Pharmaceutically acceptable modifications and derivatives" of the kinase inhibitors of the present invention include without limitation any pharmaceutically acceptable adduct or derivative, such as a prodrug, which, upon administration to a patient, is capable of providing (directly or indirectly) a kinase inhibitor as otherwise described herein. Prodrugs of the present invention include any pharmaceutically acceptable compound that yields as a metabolite any of the kinase inhibitors according to the present invention. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a prodrug is an ester which is cleaved in vivo to yield a compound of interest. Pro-drugs of a variety of compounds, and materials and methods for creating the pro-drugs from the active pharmaceutical compound, are known and may be adapted to the present invention.

Particularly favored derivatives and prodrugs of a parent compound are those derivatives and prodrugs that increase the bioavailability of the compound when administered to a mammal (e.g., by permitting enhanced absorption into the blood following oral administration) or which enhance delivery to a biological compartment of interest (e.g., the brain or lymphatic system) relative to the parent compound. Preferred prodrugs include derivatives of a compound of this invention with enhanced aqueous solubility or active transport through the gut membrane, relative to the parent compound.

The modifications and derivatives of the kinase inhibitors of the present invention also include, without limitation, PEGylation products of the kinase inhibitors, complexes and conjugates of the kinase inhibitors, and combinations thereof. Examples of the complexes of the kinase inhibitors suitable for use in the present invention include, without limitation, Protein-DNA complexes of the kinase inhibitors. Examples of the conjugates of the kinase inhibitors suitable for use in the present invention include, without limitation, protein conjugates of the kinase inhibitors.

Pharmaceutically acceptable vehicle, carrier, excipient, adjuvant, diluent and additive are used interchangeably herein and any of these terms should be viewed as a collective reference to all these categories. Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-atocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as u-, P-, and y-cyclodextrin, or chemically modified derivatives such as hydroxyalkylcyclodextrins, including 2 and 3-hydroxypropyl-cyclodextrins, or other solubilized derivatives may also be advantageously used to enhance delivery of the kinase inhibitors described herein.

Further examples of pharmaceutically acceptable carriers, which are suitable for use in the formulations of the present invention, include any and all solvents, diluents, or other vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the kinase inhibitors of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition. If desired, certain sweetening, flavoring and/or coloring agents may be added.

Further examples of carriers suitable for use in the formulations of the present invention include pharmaceutically acceptable encapsulated forms of the kinase inhibitors and their various other modifications and derivatives and include formulations utilizing liposome or microencapsulation techniques, various examples of which are known in the art. The encapsulated forms of the kinase inhibitors and their various other modifications and derivatives suitable for use in the formulations of the present invention include pharmaceutically acceptable encapsulating means selected from the group consisting of micelles, liposomes, microspheres made of biodegradable polymer, albumin microspheres, synthetic polymer encapsulants, nano-fibers, erythrocytes, virosomes, dendrimers, and combinations thereof.

In liquid or cream formulations according to the invention suitable additives include aqueous compositions including, for example at Least 30% w/w of a polyhydric alcohol such as propylene glycol, butane-1,3-diol, mannitol, sorbitol, glycerol, polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogs.

Also provided is a composition comprising at least one kinase inhibitor of the invention or its pharmaceutically acceptable derivative, and at least one pharmaceutically acceptable excipient or additive. Such compositions can be administered to a subject in need thereof to inhibit the growth, development and/or metastasis of cancers, including various forms of leukemia, including leukemias and other cancers which are resistant to other treatment, including those which are resistant to treatment with Gleevec or another kinase inhibitor, and generally for the treatment and prophylaxis of diseases or undesirable conditions mediated by one or more kinases which are inhibited by a kinase inhibitor of this invention.

The cancer treatment method of this invention involves administering (as a monotherapy or in combination with one or more other anti-cancer agents, one or more agents for ameliorating side effects, radiation, etc.) a therapeutically effective amount of a kinase inhibitor of the invention to a human or animal in need of it in order to inhibit, slow or reverse the growth, development or spread of cancer, including solid tumors or other forms of cancer such as leukemias, in the recipient. Such administration constitutes a method for the treatment or prophylaxis of diseases mediated by one or more kinases inhibited by one of the disclosed kinase inhibitors or a pharmaceutically acceptable derivative thereof. "Administration" of a kinase inhibitor of this invention encompasses the delivery to a recipient of a kinase inhibitor of the sort described herein, or a prodrug or other pharmaceutically acceptable derivative thereof, using any suitable formulation or route of administration, as discussed herein. Typically the kinase inhibitor is administered one or more times per month, often one or more times per week, e.g. daily, every other day, 5 days/week, etc. Oral and intravenous administrations are of particular current interest.

One important aspect of this invention is a method for treating cancer in a subject in need thereof, which comprises administering to the subject a treatment effective amount of a composition containing a kinase inhibitor of the sort described herein, or a prodrug or other pharmaceutically acceptable derivative thereof. Various cancers which may be thus treated are noted elsewhere herein and include, among others, cancers which are or have become resistant to another anticancer agent such as Gleevec (imatinib), Dasatinib, Nilotinib, ponatinib, or one of the other agents noted herein. Treatment may be provided in combination with one or more other cancer therapies, include surgery, radiotherapy (e.g., gamma-radiation, neutron beam radiotherapy, electron beam radiotherapy, proton therapy, brachytherapy, and systemic radioactive isotopes, etc.), endocrine therapy, biologic response modifiers (e.g., interferons, interleukins, and tumor necrosis factor (TNF) to name a few), hyperthermia, cryotherapy, agents to attenuate any adverse effects (e.g., antiemetics), and other cancer chemotherapeutic drugs. The other agent(s) may be administered using a formulation, route of administration and dosing schedule the same or different from that used with the kinase inhibitors of this invention and their derivatives.

The invention also comprises the use of a kinase inhibitor of the invention, or a pharmaceutically acceptable derivative thereof, in the manufacture of a medicament for the treatment of either acute or chronic forms of cancer (including leukemias and solid tumors, primary or metastatic, including cancers such as noted elsewhere herein and including cancers which are resistant or refractory to one or more other therapies). The kinase inhibitors of this invention and their derivatives are useful in the manufacture of an anti-cancer medicament. The kinase inhibitors of this invention and their derivatives are also useful in the manufacture of a medicament to attenuate or prevent disorders through inhibition of one or more kinases such as Src, STAT5, CrkL, Bcr-Abl, etc.

This invention further encompasses a composition comprising a kinase inhibitor of the invention, or a pharmaceutically acceptable derivative thereof, including any of the described derivatives or modifications, among others, preferably in a therapeutically-effective amount, in association with a least one pharmaceutically acceptable carrier, adjuvant or diluent.

The kinase inhibitor formulations of this invention are also useful as standards and reagents for characterizing various kinases, especially but not limited to STAT5, CrkL, Bcr-Abl and Src family kinases, as well as for studying the role of such kinases in biological and pathological phenomena; for studying intracellular signal transduction pathways mediated by such kinases, for the comparative evaluation of new kinase inhibitors; and for studying various cancers in cell lines and animal models.

This invention provides kinase inhibitors and their derivatives having biological properties which make them of interest for treating or ameliorating diseases in which kinases may be involved, symptoms of such disease, or the effect of other physiological events mediated by kinases. For instance, a number of kinase inhibitors of this invention have been shown to inhibit tyrosine kinase activity of Src and Bcr-Abl, among other tyrosine kinases which are believed to mediate the growth, development and/or metastasis of cancer. Kinase inhibitors of this invention and their derivatives have also been found to possess potent in vitro activity against cancer cell lines, including among others K-562 leukemia cells.

The kinase inhibitors of this invention and their derivatives are thus of interest for the treatment of cancers, including both primary and metastatic cancers, including solid tumors as well as lymphomas and leukemias (including CML, AML and ALL), and including cancers which are resistant to other therapies, including other therapies involving the administration of other kinase inhibitors such as Gleevec (imatinib), Dasatinib, Nilotinib, or ponatinib.

Such cancers include, among others, cancers of the breast, cervix, colon and rectum, lung, ovaries, pancreas, prostate, head and neck, gastrointestinal stroma, as well as diseases such as melanoma, multiple myeloma, non-Hodgkin's lymphoma, melanoma, gastric cancers and leukemias (e.g., myeloid, lymphocytic, myelocytic and lymphoblastic leukemias) including cases which are resistant to one or more other therapies, including among others, Gleevec (imatinib), dasatinib, nilotinib, or ponatinib.

Again, it is contemplated that the formulations of this invention, both as monotherapies and in combination therapies, will be useful against leukemias and other cancers, including those which are resistant in whole or part to other anticancer agents, specifically including Gleevec and other kinase inhibitors, and specifically including leukemias involving one or more mutations in Bcr-Abl, within or outside the kinase domain.

The method of the invention comprises administering to a subject in need thereof a therapeutically effective amount of a kinase inhibitor formulation of the invention.

A "therapeutically effective amount" is that amount effective for detectable killing or inhibition of the growth or spread of cancer cells; the size or number of tumors; or other measure of the level, stage, progression or severity of the cancer. The exact amount required will vary from subject to subject, depending on the species, age, and general condition of the subject, the severity of the disease, the particular anticancer agent, its mode of administration, combination treatment with other therapies, and the like.

The kinase inhibitors or their derivatives or compositions containing the kinase inhibitors or their derivatives, may be administered using any amount and any route of administration effective for killing or inhibiting the growth of tumors or other forms of cancer.

The anticancer formulations of the invention are preferably formulated in dosage unit form for ease of administration and uniformity of dosage. The expression "dosage unit form" as used herein refers to a physically discrete unit of anticancer agent appropriate for the patient to be treated. As is normally the case, the total daily usage of the kinase inhibitors, their derivatives, and formulations of the present invention will be decided by the attending physician using routine reliance upon sound medical judgment. The specific therapeutically effective dose level for any particular patient or organism will depend upon a variety of factors including the disorder being treated; the severity of the disorder; the potency of the specific inhibitor or derivative employed; the specific composition employed; the age, body weight, general health, sex and diet of the patient; the route and schedule of administration; the rate of metabolism and/or excretion of the inhibitor or derivative; the duration of the treatment; drugs used in combination or coincident with administration of the inhibitor or derivative of this invention; and like factors well known in the medical arts.

Furthermore, after formulation with an appropriate pharmaceutically acceptable carrier in a desired dosage, the compositions of this invention can be administered to humans and other animals orally, rectally, parenterally, intracisternally, intravaginally, intraperitoneally, topically (as by transdermal patch, powders, ointments, or drops), sublingually, bucally, as an oral or nasal spray, or the like.

The effective systemic dose of the kinase inhibitor or its derivative will typically be in the range of 0.01 to 500 mg of inhibitor or its derivative per kg of patient body weight, preferably 0.1 to 125 mg/kg, and in some cases 1 to 25 mg/kg, administered in single or multiple doses. Generally, the inhibitor may be administered to patients in need of such treatment in a daily dose range of about 50 to about 2000 mg per patient. Administration may be once or multiple times daily, weekly (or at some other multiple-day interval) or on an intermittent schedule. For example, the inhibitors of the present invention or their derivatives may be administered one or more times per day on a weekly basis (e.g. every Monday) indefinitely or for a period of weeks, e.g. 4-10 weeks. Alternatively, it may be administered daily for a period of days (e.g. 2-10 days) followed by a period of days (e.g. 1-30 days) without administration of the inhibitors of the present invention or their derivatives, with that cycle repeated indefinitely or for a given number of repetitions, e.g. 4-10 cycles. As an example, a inhibitor of the invention or its derivative may be administered daily for 5 days, then discontinued for 9 days, then administered daily for another 5 day period, then discontinued for 9 days, and so on, repeating the cycle indefinitely, or for a total of 4-10 times.

The amount of the inhibitors of the present invention or their derivatives which will be effective in the treatment or prevention of a particular disorder or condition will depend in part on well-known factors affecting drug dosage. In addition, in vitro or in vivo assays may optionally be employed to help identify optimal dosage ranges. A rough guide to effective doses may be extrapolated from dose-response curves derived from in vitro or animal model test systems. The precise dosage level should be determined by the attending physician or other health care provider and will depend upon well-known factors, including route of administration, and the age, body weight, sex and general health of the individual; the nature, severity and clinical stage of the disease; the use (or not) of concomitant therapies; and the nature and extent of genetic engineering of cells in the patient.

When administered for the treatment or inhibition of a particular disease state or disorder, the effective dosage of the inhibitors of the present invention or their derivatives may vary depending upon the particular compound utilized, the mode of administration, the condition, and severity thereof, of the condition being treated, as well as the various physical factors related to the individual being treated. In many cases, satisfactory results may be obtained when the compound is administered in a daily dosage of from about 0.01 mg/kg-500 mg/kg, preferably between 0.1 and 125 mg/kg, and more preferably between 1 and 25 mg/kg. The projected daily dosages are expected to vary with route of administration. Thus, parenteral dosing will often be at levels of roughly 10% to 20% of oral dosing levels.

When the inhibitors of the present invention or their derivatives are used as part of a combination regimen, dosages of each of the components of the combination are administered during a desired treatment period. The components of the combination may administered at the same time; either as a unitary dosage form containing both components, or as separate dosage units; the components of the combination can also be administered at different times during a treatment period, or one may be administered as a pretreatment for the other.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use. The term "prodrug" refers to compounds that are transformed in vivo to yield the parent compound of the above formula, for example by hydrolysis in blood. See, e.g., T. Higuchi and V. Stella, Pro-drugs as Novel Delivery Systems, Vol. 14 of the A.C.S. Symposium Series, and Edward B. Roche, ed., Bioreversible Carriers in Drug Design, American Pharmaceutical Assocn. and Pergamon Press, 1987, both of which are incorporated herein by reference.

Compositions are provided which comprise any one of the kinase inhibitors of the present invention described herein (or a prodrug, or any other pharmaceutically acceptable derivative thereof) and one or more pharmaceutically acceptable carriers or excipients. These compositions optionally further comprise one or more additional therapeutic agents. Alternatively, a compound of this invention may be administered to a patient in need thereof in combination with the administration of one or more other therapeutic regimens (e.g. Gleevec or other kinase inhibitors, interferon, bone marrow transplant, farnesyltransferase inhibitors, bisphosphonates, thalidomide, cancer vaccines, hormonal therapy, antibodies, radiation, etc.). For example, additional therapeutic agents for conjoint administration or inclusion in a pharmaceutical composition with a kinase inhibitor of this invention or its derivative may be another one or more anticancer agents.

This invention also encompasses a class of compositions comprising the active compounds of this invention in association with one or more pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The kinase inhibitors of the present invention, or their derivatives, and the compositions of the present invention may, for example, be administered orally, mucosally, topically, rectally, pulmonarily such as by inhalation spray, or parentally including intravascularly, intravenously, intraperitoneally, subcutaneously, intramuscularly, intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient.

Examples of such dosage units are tablets or capsules. For example, these may contain an amount of active ingredient from about 1 to 2000 mg, preferably from about 1 to 500 mg, more commonly from about 5 to 200 mg. A suitable daily dose for a human or other mammal may vary depending on the condition of the patient and other factors, but, once again, can be determined using routine methods.

The amount of the kinase inhibitors of the present invention or their derivatives which are administered and the dosage regimen for treating a disease condition with the kinase inhibitors of the present invention or their derivatives and/or compositions of this invention depends on a variety of factors, including the age, weight, sex and medical condition of the subject, the type of disease, the severity of the disease, the route and frequency of administration, and the particular inhibitor or derivative employed. Thus, the dosage regimen may vary widely, but can be determined routinely using standard methods. A typical daily dose is in the range of 0.01 to 500 mg of compound per kg body weight, preferably between 0.1 and 125 mg/kg body weight and in some cases between 1 and 25 mg/kg body weight. As mentioned previously, the daily dose can be given in one administration or may be divided between 2, 3, 4 or more administrations.

For therapeutic purposes, the active kinase inhibitors of the present invention or their derivatives are ordinarily combined with one or more adjuvants, excipients or carriers appropriate to the indicated route of administration. If administered by mouth, the kinase inhibitors of the present invention or their derivatives may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, *acacia* gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. In the case of skin conditions, it may be preferable to apply a topical preparation of compounds of this invention to the affected area two to four times a day. Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The kinase inhibitors of the present invention or their derivatives can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The oily phase of the emulsions of this invention may be constituted from known ingredients in a known manner.

While the liquid phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. Together, the emulsifier(s) with or without stabilizer(s) make-up the so called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required.

Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients.

The active ingredients are preferably present in such formulations in a concentration of 0.5 to 20%, advantageously 0.5 to 10% and particularly about 1.5% w/w. Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Pharmaceutical compositions of this invention comprise one or more kinase inhibitors of the present invention or their derivatives; an additional agent selected from other kinase inhibitory agents, an immunosuppressant, other anticancer agents, an anti-viral agent, anti-inflammatory agent, antifungal agent, antibiotic, or an anti-vascular hyperproliferation compound; and any pharmaceutically acceptable carrier, adjuvant or vehicle.

The term "pharmaceutically acceptable carrier or adjuvant" refers to a carrier or adjuvant that may be administered to a patient, together with the kinase inhibitors of the present invention or their derivatives, and which does not destroy the pharmacological activity thereof and is nontoxic when administered in doses sufficient to deliver a therapeutic amount of the kinase inhibitors of the present invention or their derivatives.

The pharmaceutical compositions may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase that is combined with emulsifying and/or suspending agents.

The pharmaceutical compositions may be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents, examples of which are also well known in the art.

While the kinase inhibitors of the present invention or their derivatives can be administered as the sole active pharmaceutical agent, they can also be used in combination with one or more other kinase inhibitors of the present invention or their derivatives or with one or more other agents. When administered as a combination, the therapeutic agents can be formulated as separate compositions that are administered at the same time or sequentially at different times, or the therapeutic agents can be given as a single composition.

The phrase "combination therapy", in referring to the use of the kinase inhibitors of the present invention or their derivatives together with another pharmaceutical agent, means the coadministration of each agent in a substantially simultaneous manner as well as the administration of each agent in a sequential manner, in either case, in a regimen that will provide beneficial effects of the drug combination. Coadministration includes inter alia the simultaneous delivery, e.g., in a single tablet, capsule, injection or other dosage form having a fixed ratio of these active agents, as well as the simultaneous delivery in multiple, separate dosage forms for each agent respectively.

Thus, the administration of the kinase inhibitors of the present invention or their derivatives may be in conjunction with additional therapies known to those skilled in the art in the prevention or treatment of cancer, such as radiation therapy or cytostatic agents, cytotoxic agents, other anticancer agents and other drugs to ameliorate symptoms of the cancer or side effects of any of the drugs.

If formulated as a fixed dose, such combination products employ the kinase inhibitors of the present invention or their derivatives within the accepted dosage ranges. The kinase inhibitors of the present invention or their derivatives may also be administered sequentially with other anticancer or cytotoxic agents when a combination formulation is inappropriate. The invention is not limited in the sequence of administration; the kinase inhibitors of the present invention or their derivatives may be administered prior to, simultaneously with, or after administration of the other anticancer or cytotoxic agent.

It is to be understood that the present invention is not limited to the embodiments described above, but encompasses any and all embodiments within the scope of the following claims.

The invention claimed is:

1. A formulation having kinase inhibitor activity, the formulation comprising:
   a first component selected from the group consisting of compounds having a formula in accordance with the following:

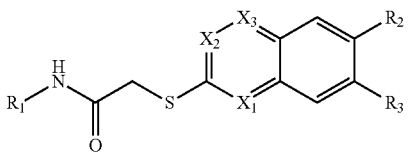

wherein $R_1$ is selected from the group consisting of:
a) an aromatic ring substituted with a group selected from groups consisting of alkyl, alkoxy, —COOX$_4$ wherein X$_4$ is selected from H and an alkyl group with one to ten carbon atoms, nitrile groups, and halides, excluding said aromatic ring being solely substituted with a O—CH$_3$ group at the para position relative to the bond between the aromatic ring and the nitrogen,
b) a heterocyclic ring substituted with a group selected from groups consisting of alkyl, alkoxy, —COOX$_4$ wherein X$_4$ is selected from H and an alkyl group with one to ten carbon atoms, nitrile groups, and halides, and
c) a first ring selected from an aromatic ring and a heterocyclic ring, said first ring being linked to a second ring selected from an aromatic ring and a heteroaromatic ring, said first ring being substituted with a group selected from groups consisting of alkyl, alkoxy, —COOX$_4$ wherein X$_4$ is selected from H and an alkyl group with one to ten carbon atoms, nitrile groups, and halides,
wherein $R_2$ is selected from H and OX$_5$ where X$_5$ is selected from an alkyl group with one to ten carbon atoms, the radical —CH$_2$—, and the radical —CH$_2$CH$_2$—,
wherein $R_3$ is selected from H and OX$_6$ where X$_6$ is selected from an alkyl group with one to ten carbon atoms, the radical —CH$_2$—, and the radical —CH$_2$CH$_2$—,
wherein $X_1$ is selected from —CH—, —C(=O)—, and N,
wherein $X_3$ is selected from —CH—, —C(=O)—, and N,
wherein $X_2$ is selected from N, —O(X$_7$)— where X$_7$ is selected from H, an alkyl group with one to ten carbon atoms, an alkoxy group, a nitrile, and a halide,
pharmaceutically acceptable derivatives of said compounds, and mixtures thereof; and
a pharmaceutically acceptable delivery vehicle.

2. The formulation according to claim 1, wherein said first ring is directly linked to said second ring.

3. The formulation according to claim 1, wherein said first ring is linked to said second ring through an amide bond.

4. The formulation according to claim 1, wherein said second ring is substituted with a group selected from groups consisting of alkyl, alkoxy, —COOX$_4$ wherein X$_4$ is selected from H and an alkyl group with one to ten carbon atoms, nitrile groups, and halides.

5. The formulation according to claim 1, wherein at least one of said first ring and said second ring has a basic group attached to improve solubility.

6. The formulation according to claim 1, wherein X$_5$ is selected from the radicals —CH$_2$— and —CH$_2$CH$_2$—, wherein X$_6$ is selected from the radicals —CH$_2$— and —CH$_2$CH$_2$—, and X$_5$ and X$_6$ are linked together to form a heterocycle.

7. A formulation according to claim 1, wherein said first component is selected from the group consisting of compounds having a formula as follows:

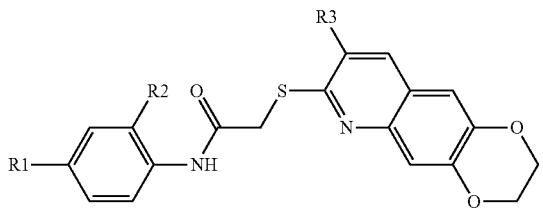

wherein R1 is selected from the group consisting of H, O—CH$_3$, and COO—CH$_3$, wherein R2 is selected from the group consisting of O—CH$_3$, CH$_3$, F, and H, wherein R3 is selected from the group consisting of CH$_2$—CH$_3$, CH$_3$, and C≡N, except that R1 may not be O—CH$_3$ when R2 is H,
derivatives of said compounds, and mixtures thereof.

8. The formulation according to claim 7, wherein said derivatives of said compounds are selected from the group consisting of PEGylation products of said compounds, encapsulated forms of said compounds, encapsulated forms of said PEGylation products, complexes of said compounds, encapsulated forms of said complexes, conjugates of said compounds, encapsulated forms of said conjugates, prodrugs of said compounds, encapsulated forms of said prodrugs, and combinations thereof.

9. The formulation according to claim 8, wherein said complexes or conjugates of said compounds are selected from protein-DNA complexes of said compounds, protein conjugates of said compounds, and mixtures thereof.

10. A method of inhibiting kinase activity in inflammatory cells, the method comprising the steps of:
providing a kinase inhibitor formulation according to claim 1; and
introducing the kinase inhibitor formulation to one or more inflammatory cells to thereby inhibit one or more kinases involved in one or more cell signaling pathways involved in progression of an inflammatory disease.

11. The formulation according to claim 8, wherein each of said encapsulated forms of said compounds, said encapsulated forms of said PEGylation products, said encapsulated forms of said complexes, and said encapsulated forms of said conjugates is formed using any encapsulation means selected from the group consisting of encapsulation by micelles, encapsulation by liposomes, encapsulation by microspheres made of biodegradable polymer, encapsulation by albumin microspheres, encapsulation by synthetic polymers, encapsulation by nanofibers, encapsulation by multifunctional inorganic nanoparticles, encapsulation by erythrocytes, encapsulation by virosomes, encapsulation by dendrimers, and combinations thereof.

12. The formulation in accordance with claim 1, wherein said first component is at least in part encapsulated using a pharmaceutically acceptable encapsulation means selected from the group consisting of micelles, liposomes, microspheres made of biodegradable polymer, albumin microspheres, synthetic polymer encapsulants, nanofibers, multifunctional inorganic nanoparticles, erythrocytes, virosomes, dendrimers, and combinations thereof.

13. The formulation according to claim 7, wherein R1 is H, R2 is CH$_3$, and R3 is CH$_2$—CH$_3$.

14. A method of inhibiting kinase activity in cancer cells, the method comprising the steps of:
providing a kinase inhibitor formulation according to claim 1; and introducing the kinase inhibitor formulation to one or more cancer cells to thereby inhibit one or more kinases involved in one or more cell signaling pathways involved in progression of cancer.

15. A method of inhibiting kinase activity in cancer cells, the method comprising the steps of:
   providing a kinase inhibitor formulation according to claim 7; and
   introducing the kinase inhibitor formulation to one or more cancer cells to thereby inhibit one or more kinases involved in one or more cell signaling pathways involved in progression of cancer.

16. A method of inhibiting kinase activity in inflammatory cells, the method comprising the steps of:
   providing a kinase inhibitor formulation according to claim 7; and
   introducing the kinase inhibitor formulation to one or more inflammatory cells to thereby inhibit one or more kinases involved in one or more cell signaling pathways involved in progression of an inflammatory disease.

17. The formulation in accordance with claim 1, wherein said pharmaceutically acceptable delivery vehicle is selected from the group consisting of cyclodextrins and mixtures thereof.

* * * * *

UNITED STATES PATENT AND TRADEMARK OFFICE
CERTIFICATE OF CORRECTION

PATENT NO. : 9,636,340 B2  
APPLICATION NO. : 14/537980  
DATED : May 2, 2017  
INVENTOR(S) : Ayyappan K. Rajasekaran Page 1 of 1

It is certified that error appears in the above-identified patent and that said Letters Patent is hereby corrected as shown below:

In the Specification

Column 3, Line 24, change "X3" to -- X2 --

Column 3, Line 25, change "X2" to -- X3 --

Column 4, Line 17, change "C = N" to -- C ≡ N --

In the Claims

Column 31, Line 42, change "—O(X7)—" to -- —C(X7)— --

Column 32, Line 15, change "C E N" to -- C ≡ N --

Signed and Sealed this  
Eighth Day of May, 2018

Andrei Iancu  
*Director of the United States Patent and Trademark Office*